(12) United States Patent
Nakakado et al.

(10) Patent No.: US 8,002,928 B2
(45) Date of Patent: Aug. 23, 2011

(54) METHOD AND APPARATUS FOR PRODUCING WEARING ARTICLE

(75) Inventors: Masaki Nakakado, Settsu (JP); Yuzo Ichiura, Settsu (JP); Satoshi Tanaka, Settsu (JP); Ikuo Tachibana, Settsu (JP)

(73) Assignee: Zuiko Corporation, Osaka (JP)

( * ) Notice: Subject to any disclaimer, the term of this patent is extended or adjusted under 35 U.S.C. 154(b) by 727 days.

(21) Appl. No.: 11/180,170

(22) Filed: Jul. 13, 2005

(65) Prior Publication Data
US 2005/0241751 A1 Nov. 3, 2005

Related U.S. Application Data

(63) Continuation of application No. 10/316,523, filed on Dec. 11, 2002, now Pat. No. 7,008,497.

(30) Foreign Application Priority Data

Aug. 22, 2002 (JP) ................. 2002-241959
Oct. 28, 2002 (JP) ................. 2002-312403

(51) Int. Cl.
*B32B 15/00* (2006.01)
(52) U.S. Cl. ................. 156/229; 156/250; 156/267
(58) Field of Classification Search ........... 156/229, 156/250, 267
See application file for complete search history.

(56) References Cited

U.S. PATENT DOCUMENTS

| | | | |
|---|---|---|---|
| 3,828,367 A | 8/1974 | Bourgeois | |
| 4,171,239 A * | 10/1979 | Hirsch et al. | 156/461 |
| 4,425,173 A | 1/1984 | Frick | |
| 4,488,923 A | 12/1984 | Pieniak | |
| 4,506,779 A | 3/1985 | Seragnoli | |
| 4,578,133 A | 3/1986 | Oshefsky et al. | |
| 4,610,751 A | 9/1986 | Eschler | |
| 4,726,876 A | 2/1988 | Tomsovic, Jr. | |
| 4,767,487 A | 8/1988 | Tomsovic, Jr. | |
| 4,880,102 A | 11/1989 | Indrebo | |
| 4,895,568 A | 1/1990 | Enloe | |
| 5,025,910 A | 6/1991 | Lasure et al. | |
| 5,143,679 A * | 9/1992 | Weber et al. | 264/288.8 |
| 5,525,175 A | 6/1996 | Blenke et al. | |

(Continued)

FOREIGN PATENT DOCUMENTS

EP 0 805 116 A1 11/1997

(Continued)

OTHER PUBLICATIONS

European Search Report for corresponding Application No. 01 12 8318 dated Jun. 20, 2002.
THK LM System, R Guide HCR Type, THK Co., Ltd. Catalog No. 154-2, Publication Date Nov. 10, 1996, 4 pages.
THK LM System, General Catalog (No. 300-6), TNK Co., Ltd. Publication Date Apr. 30, 2000, 3 pages.

(Continued)

*Primary Examiner* — Kimberly K McClelland
(74) *Attorney, Agent, or Firm* — Renner, Otto, Boisselle & Sklar, LLP

(57) ABSTRACT

A method for producing a wearing article of the present invention includes the steps of: supplying an elastic member; stretching the elastic member; placing the stretched elastic member so that the elastic member spreads across a plurality of first webs divided in a transport direction; making a part of a second web loose in the transport direction while transporting the second web, thereby forming a loose portion; placing the first webs, on which the elastic member is disposed, on non-loose portions before and after the loose portion of the second web; and cutting the elastic member between adjacent first webs of the plurality of first webs.

16 Claims, 28 Drawing Sheets

U.S. PATENT DOCUMENTS

| | | | |
|---|---|---|---|
| 5,612,118 A | 3/1997 | Schleinz et al. | |
| 5,622,581 A | 4/1997 | Ducker et al. | |
| 5,660,657 A | 8/1997 | Rajala et al. | |
| 5,711,832 A | 1/1998 | Glaug et al. | |
| 5,964,970 A * | 10/1999 | Woolwine et al. | 156/64 |
| 6,022,443 A | 2/2000 | Rajala et al. | |
| 6,217,690 B1 | 4/2001 | Rajala et al. | |
| 6,554,815 B1 | 4/2003 | Umebayashi | |
| 6,730,188 B2 * | 5/2004 | Sanders | 156/256 |
| 6,748,996 B2 | 6/2004 | Nakakado et al. | |
| 7,008,497 B2 * | 3/2006 | Nakakado et al. | 156/229 |
| 2002/0046802 A1 * | 4/2002 | Tachibana et al. | 156/209 |
| 2002/0103468 A1 | 8/2002 | Nakakado et al. | |
| 2002/0125105 A1 | 9/2002 | Nakakado | |

FOREIGN PATENT DOCUMENTS

| | | |
|---|---|---|
| EP | 0 974 323 | 7/1998 |
| GB | 2 214 202 | 8/1989 |
| JP | 1272803 | 10/1989 |
| JP | 63317576 | 12/1998 |
| JP | 2000-026015 | 1/2000 |
| JP | 2001-061890 | 3/2001 |
| WO | 98/00356 | 1/1998 |
| WO | 00/76444 | 12/2000 |

OTHER PUBLICATIONS

NB Slide Way, Gonio Way RV Type (No. 4010), Nippon Bearing Co., Ltd., Publication Date May 5, 2000, 4 pages.

THK LM System, R Guide HCR Type, THK Co., Ltd. Catalog No. 154-2, Publication Date Nov. 10, 1996, 4 pages. (provided in U.S. Appl. No. 09/995,053).

THK LM System, General Catalog (No. 300-6), THK Co., Ltd. Publication Date Apr. 30, 2000, 3 pages. (provided in U.S. Appl. No. 09/995,053).

NB Slide Way, Gonio Way RV Type (No. 4010), Nippon Bearing Co., Ltd., Publication Date May 5, 2000, 4 pages. (provided in U.S. Appl. No. 09/995,053).

THK LM System, R Guide HCR Type, THK Co., Ltd. Catalog, pp. a-482-a-483.

NB Slide Way, Gonio Way RV Type, Nippon Bearing Co., Ltd., pp. G-62-G-63.

NB Slide Way, Gonio Way RV Type, Nippon Bearing Co., Ltd., pp. G-64-G-65.

NB Slide Way, Gonio Way RV Type, Nippon Bearing Co., Ltd., pp. G-66-G-67.

* cited by examiner

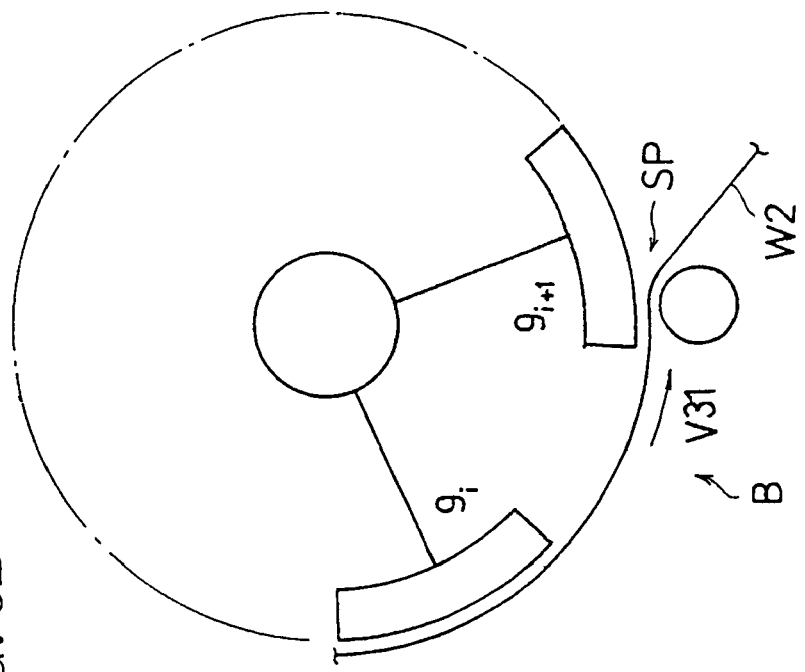
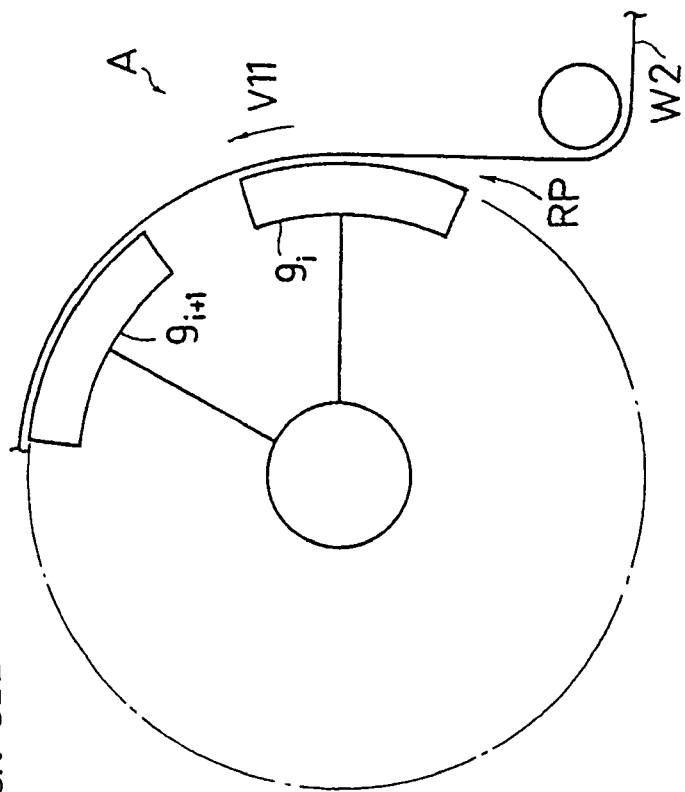
FIG. 5A
FIG. 5B

② Attachment state of an absorber

③ Both-end folded state

④ Two-folded state

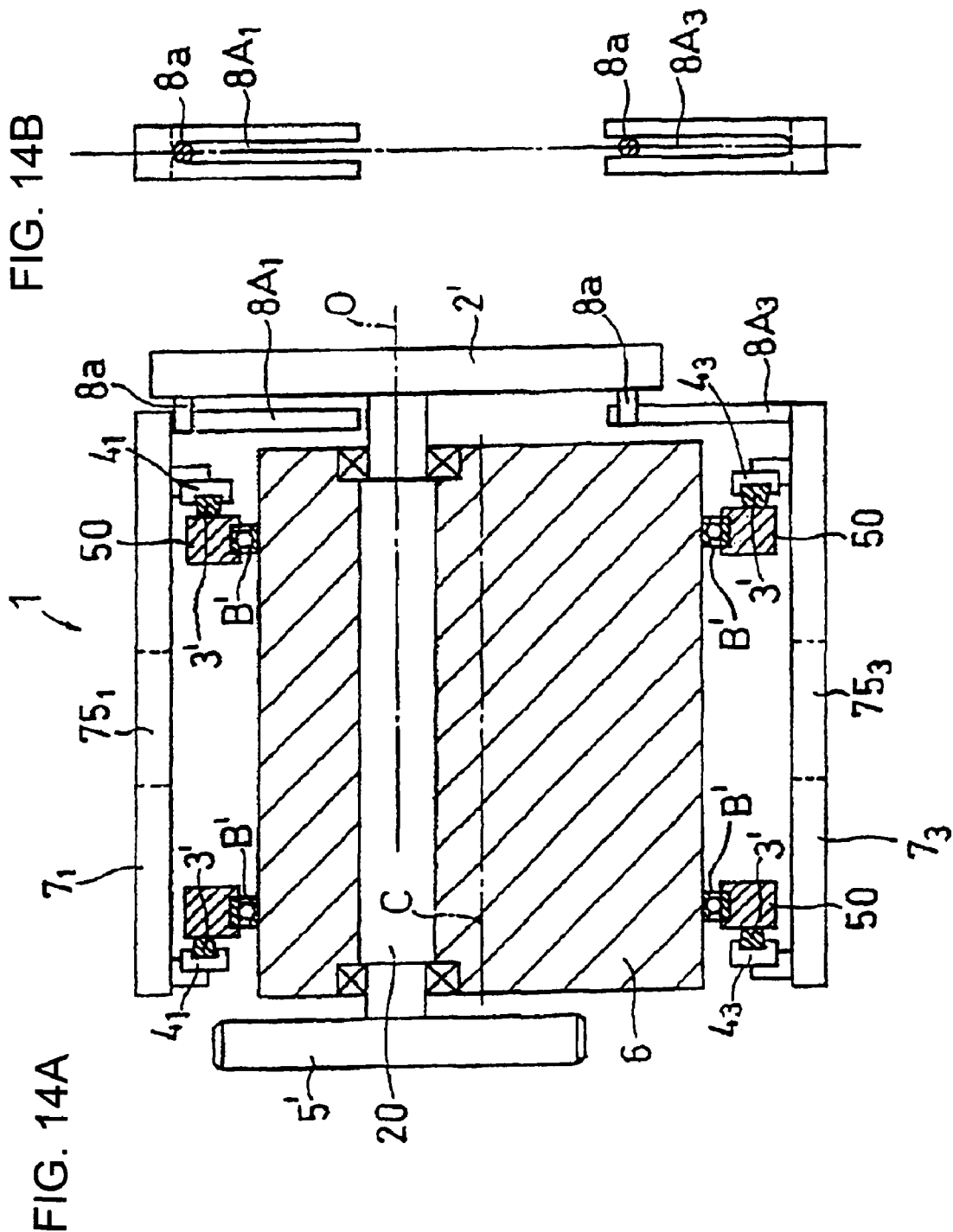

FIG. 19A
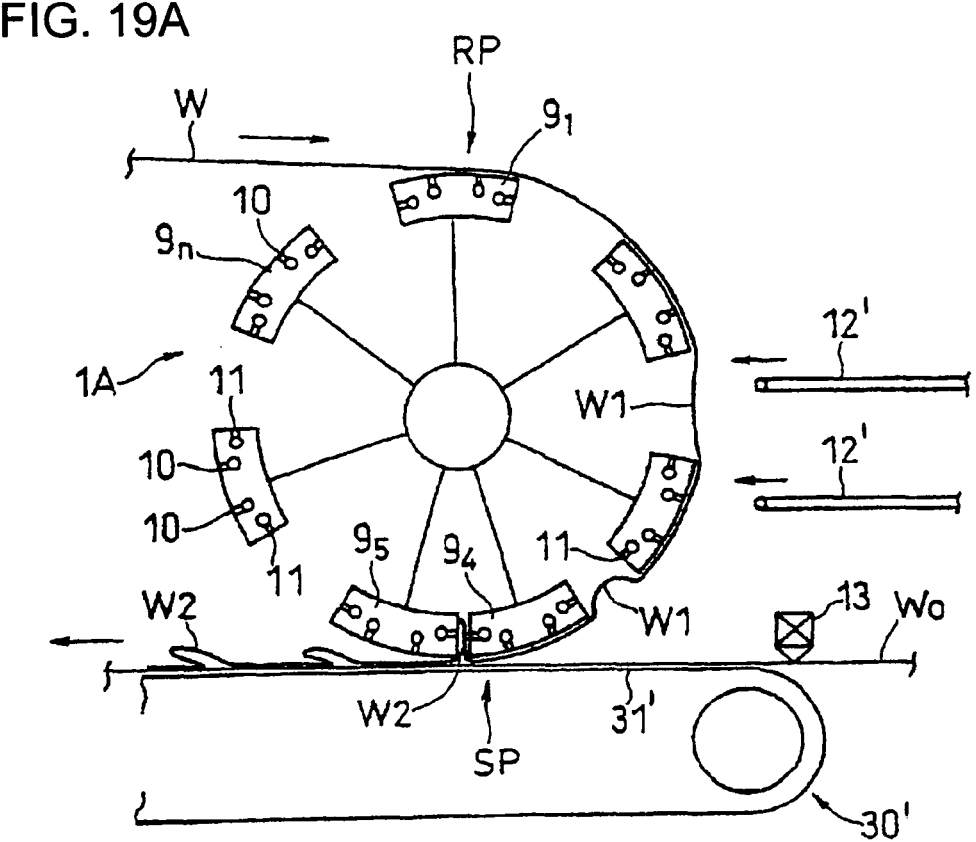
FIG. 19B
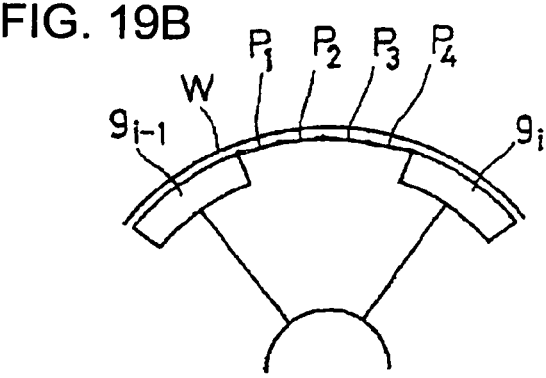
FIG. 19C
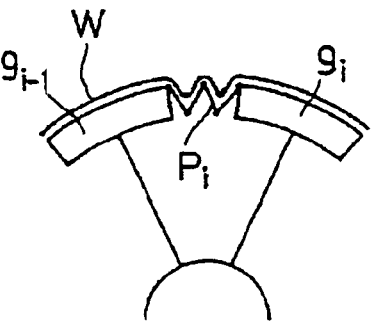
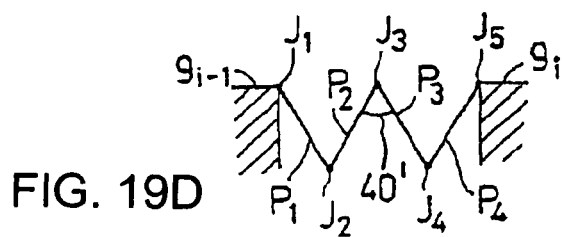
FIG. 19D

METHOD AND APPARATUS FOR PRODUCING WEARING ARTICLE

CROSS-REFERENCE TO RELATED APPLICATION

The present application is a continuation of commonly assigned, application Ser. No. 10/316,523, filed Dec. 11, 2002, now U.S. Pat. No. 7,008,497 and entitled "Method and Apparatus for Producing Wearing Article", the entire disclosure of which is incorporated herein by reference.

BACKGROUND OF THE INVENTION

1. Field of the Invention

The present invention relates to a method and apparatus for producing a disposable wearing article such as paper diapers and pants.

2. Description of the Related Art

In the above-mentioned type of wearing articles, in order to form, for example, a waist gathering, an elastic member is placed on a sheet surface. However, such an elastic member allows an absorber to shrink, so that the absorber becomes stiff, degrading a feeling of wearing.

As a prior art of cutting an elastic member, Japanese Laid-Open Patent Publication No. 2001-224627 discloses a method for interposing a film sheet for gathering between a peripheral surface of an adsorbent roller and a cutter blade of a cutter roller, and cutting the film sheet.

Furthermore, International publication No. WO 00/04855 discloses a method for forming a web loop.

Japanese Laid-Open Patent Publication No. 63-317576, for example, discloses a movement of a plurality of pads rotating about a predetermined axis while each of the pads changes its velocity, during a process of producing a worn article or a web (a continuous material). Japanese National Phase PCT Laid-Open Publication No. 2000-514024 discloses a material engagement member reciprocating in a direction parallel to a rotation axis of a drum.

When each of the pads is supported by a bearing, the same number of bearings as the number of pads are required so that the velocities of the pads can be changed individually, thereby increasing the size and/or complexity of the device.

SUMMARY OF THE INVENTION

In view of the problem in the prior art, it is an object of the present invention to provide a rotation device having a simple structure and being capable of providing a complicated movement. It is also an object of the present invention to provide a method for transferring a worn article, a method for folding a web and a device for folding a web that can suitably employ the rotation device, and a disposable worn article produced by using the same.

In order to achieve the objects set forth above, a first rotation device of the present invention includes: an endless guide; a plurality of moving sections that slide while being guided by the guide; and a rotation member that allows the guide to rotate about an axis. In addition, the plurality of moving sections are arranged in the rotation allowance direction of the rotation member; and the plurality of moving sections can slide in the direction of rotation of the rotation member or in the opposite direction by being guided by the guide.

A second rotation device of the present invention includes: a plurality of guides; a plurality of moving sections that slide while being guided by the plurality of guides; and a rotation member that allows the plurality of guides to rotate about an axis. Furthermore each of the moving sections is guided by at least one of the guides; and the plurality of guides is provided about the axis so as to be arranged in the rotation allowance direction of the rotation member while surrounding the axis, so that the plurality of moving sections can slide in the direction of rotation of the rotation member or the opposite direction.

As a rotational force having a predetermined velocity curve is applied to the moving sections, the rotation member rotates at a high velocity along with the rotation of the moving sections. Meanwhile, each moving section rotates with respect to the guide at a low relative velocity. In this way, the friction between the moving sections and the guide is significantly reduced, thereby improving the durability of the device.

Ideally, the rotation member is capable of an unlimited rotation, and may be a ball bearing or a roller bearing including a rolling element such as a ball or a roller.

The guide may be any type of guide as long as it allows the sliding movement of the moving sections in a direction including a component of the rotation allowance direction of the rotation member. The term "endless guide" as used herein refers to not only a generally completely ring-shaped guide, but also to those having slight gaps in the circumferential direction, or even to those obtained by arranging guide elements, which together form one guide, so as to be spaced apart from one another at a predetermined interval. Moreover, the guide elements may overlap with one another as viewed in the axial direction. The phrase "in a direction including a component of the rotation allowance direction of the rotation member" as used herein means that a guide element may be provided in an inclined direction. The guide element may be a rail or a groove.

In the second rotation device of the present invention, the phrase "a plurality of guides" means that the guides are spaced apart from one another in the direction of rotation or in the axial direction to such a degree that a moving section cannot move from one guide to another.

Where one moving section moves from one of a plurality of guide elements to another, the plurality of guide elements together form one guide.

In the present invention, it is preferred to provide a controller for controlling the moving velocity of the moving sections. Such a controller causes the moving sections to rotate at differing predetermined instantaneous velocities, thereby changing the pitch between the moving sections during rotation.

The term "instantaneous velocity" as used herein refers to a velocity in a minute period of time, meaning that each moving section rotates while changing its velocity depending on the rotational position thereof.

The present invention can be used with a rotation device as described in PCT International Publication WO01/44086, a method for transferring worn articles while changing the pitch thereof, a method for folding a web, or a device for folding a web.

A method for folding a web of the present invention is a method for folding a web by using a rotation device including a plurality of pads that rotate about a predetermined axis so as to continuously transfer the web. The method includes: supplying the web onto surfaces of the rotation device pads; rotating adjacent ones of the pads onto which the web has been supplied so as to change the interval therebetween to slacken a portion of the web between the adjacent pads, thereby folding the portion of the web; and releasing the web from the pads.

Such a folding method can be realized using the first or second rotation devices of the present invention. Other rotation devices such as that described in PCT International Publication WO01/44086 may be used in place of the rotation device including a plurality of pads.

A device for folding a web of the present invention is a device for folding a web to form a wall in a direction transverse to a web running direction. The device includes: a transfer member for forming a slack portion in the web in the running direction thereof while continuously transferring the web; and a member for folding the slack portion so as to form the wall.

The term "wall" as used in the present invention refers to a portion of a web or a sheet-like material that has been folded, regardless of whether the wall is laid down along the surface of the web or standing on the web.

In the folding device of the present invention, the "transfer member" may be any member including a plurality of transfer sections for transferring the web in the web running direction, wherein the transfer velocity of one of the transfer sections is set to be lower than that of another transfer section upstream of the one of the transfer sections so as to form a slack portion in a portion of the web between the upstream and downstream transfer sections.

In the present invention, it is preferred to provide a directioning member for defining the direction in which a slack portion is to be folded.

In the present invention, the term "slack portion" refers to a portion of a web on which no tension is applied.

In the present invention, it is preferred to provide a fold-holding section for maintaining the shape or condition of a folded portion obtained by folding the slack portion.

BRIEF DESCRIPTION OF THE DRAWINGS

FIGS. 5A and 5B are partial side views showing a circumferential velocity of pads.

FIG. 14A is a schematic cross-sectional view illustrating a second embodiment of the rotation device of the present invention.

FIG. 14B is a side view illustrating a portion of a fixed pin and groove arrangement for controlling a rotational velocity of a bridging section according to the second embodiment of the invention.

FIG. 19A is a schematic view illustrating a variation of a folding device.

FIG. 19B is a diagram illustrating plates between two pads being in a spread formation.

FIG. 19C is a diagram illustrating plates being folded into a bellows-like shape.

FIG. 19D is an enlarged view illustrating plates between two pads.

DESCRIPTION OF THE PREFERRED EMBODIMENTS

Hereinafter, the present invention will be described by way of illustrative embodiments with reference to the drawings.

Embodiment 1

FIGS. 1 to 5A-B show Embodiment 1.

Figure 1:
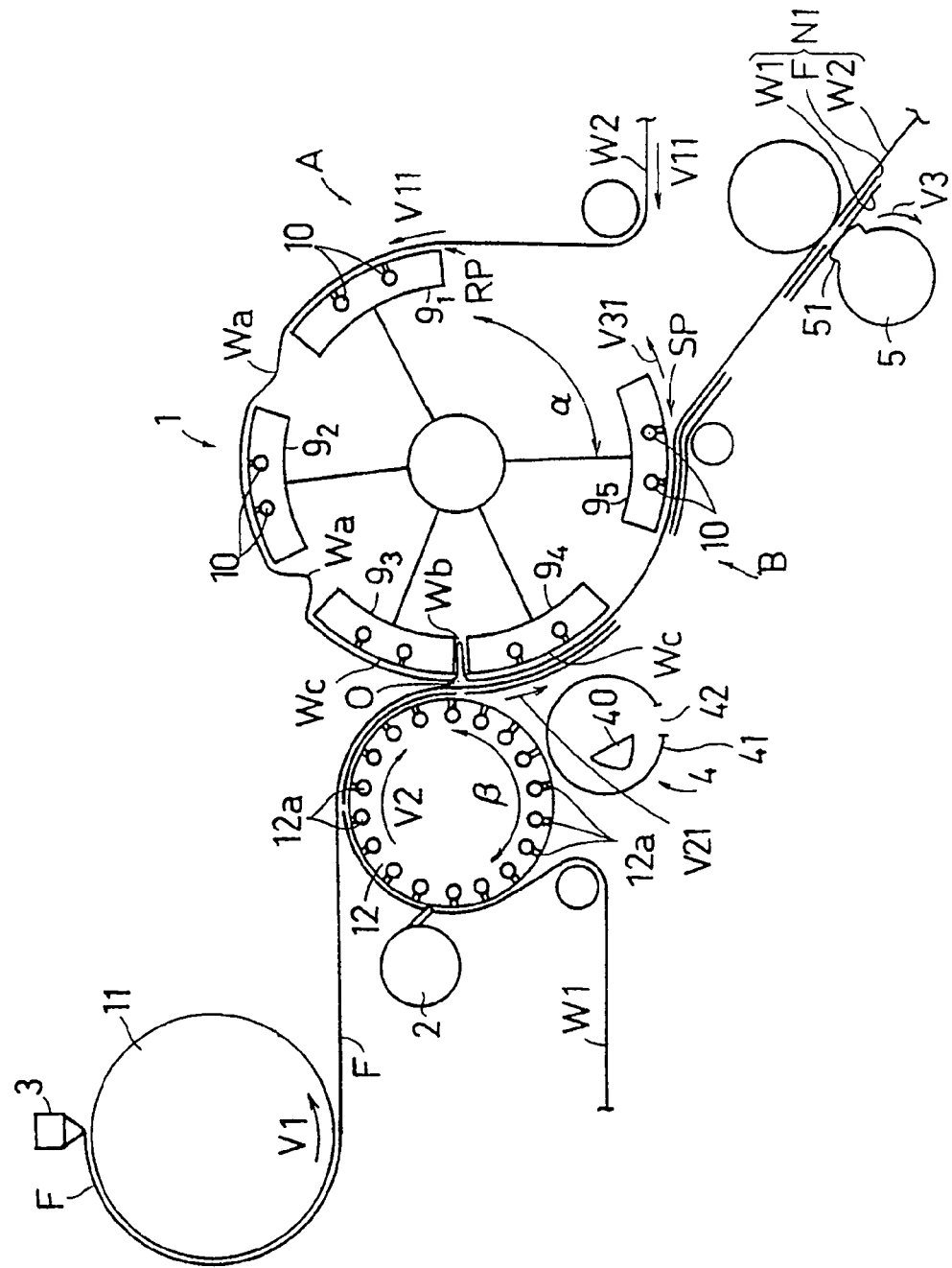
FIG. 1 is a side layout view of an apparatus for producing a wearing article of Embodiment 1 according to the present invention.

An apparatus for producing a wearing article shown in FIG. 1 is capable of providing a web with looseness and intermittently placing an elastic member on at least a part of the web. For example, the apparatus for producing a wearing article includes a rotation apparatus 1 capable of providing a second web W2 with looseness and a second roller 12 capable of placing an elastic member F on portions of the second web W2 other than those which are loose. When the elastic member F extending across a loose portion of the second web W2 is cut with at least one of a laser, an industrial light, a blade, and scissors, the apparatus can intermittently place the elastic member F on the second web W2. This intermittent placement is mainly caused by the looseness of the second web W2. Hereinafter, the configuration and operation of the rotation apparatus 1, the second roller 12, and the like will be described.

In FIG. 1, a supply apparatus 3 of the elastic member F supplies the elastic member F to the surface of a first roller 11. The elastic member F on the first roller 11 is fed to the second roller 12. A circumferential velocity V2 of the second roller 12 is set to be larger than a circumferential velocity V1 of the first roller 11. Therefore, the elastic member F is stretched between the first roller 11 and the second roller 12.

The second roller 12 is supplied with a first web W1. The second roller 12 transports the first web W1 while sucking the first web W1 by vacuum suction or the like. On the surface of the second roller 12, for example, a number of suction holes 12a for sucking the first web W1 may be provided. After the first web W1 is sucked to be held on the surface of the second roller 12 by vacuum suction or the like, the first web W1 is divided into a predetermined size with a web cutter 2. In this division, the first web W1 may be cut or half-cut to a predetermined length in a transport direction. In the case where the first web W1 is half-cut, the first web W1 may be cut to a predetermined length together with the elastic member F in a subsequent step or cut in a predetermined length when an interval of pads is increased. After this division, the elastic member F is placed so as to spread across the surface of the respective first webs W1. In the case where the elastic member F is made of thread rubber or flat rubber, an adhesive is applied to at least one of the elastic member F, the first web W1, and the second web.

It may also be possible that after the elastic member F is placed on the first web W1, the elastic member F is cut together with the first web W1. Furthermore, in the case where the elastic member F is made of hot-melt resin, molten resin discharged from the supply apparatus 3 is cooled by the first roller 11. The molten resin may be cooled with cool water. Furthermore, the first roller 11 may be a porous roller. In the case where the first roller 11 is a porous roller, the first roller 11 may be configured so that air is discharged from the inside of the first roller 11 through holes. Due to the air, the hot-melt resin becomes unlikely to adhere to the roller. When the air is discharged from the porous body, the volume of the air is increased to cool the roller. Thus, the hot-melt resin can be cooled. The porous roller may be formed by sintering stainless ball or the like.

Furthermore, it may also be possible that the first roller 11 is provided with grooves or the like, whereby resin is molded. For example, mesh-shaped (for example, lattice-shaped) grooves are formed on the first roller 11, and hot-melt resin is applied to the grooves of the first roller 11 with a coater or the like, whereby a mesh-shaped elastic member is formed.

When hot-melt resin having a softening point lower than that of Lycra® is used as the elastic member, the subsequent cutting step becomes easier, compared with the case of using Lycra®.

The hot-melt resin may be a kneaded composition and may comprise a thermoplastic resin, tackifier, viscosity adjuster, antioxidant, heat stabilizer, ultraviolet radiation absorbent, bulking agent, elasticizer, and the like. The thermoplastic resin may include elastomers such as olefins {EVA (ethylene-vinyl acetate copolymer), APAO (amorphous-poly-α-olefin)}, rubbers {SIS (styrene-isoprene-styrene copolymer), SBS (styrene-butadiene-styrene copolymer), SEBS (styrene-ethylene-butadiene-styrene copolymer), SEPS (styrene-ethylene-propylene-styrene copolymer)}, polyamides and polyesters. The thermoplastic resin may be a single elastomer or a blend of more than one elastomer.

The rotation apparatus 1 for folding is placed in the vicinity of the second roller 12. The rotation apparatus 1 has a plurality of pads 9 capable of sucking the second web W2 and transporting it. On the surface of a pad $9_i$, suction holes 10 for sucking the second web W2 are provided. The rotation apparatus 1 continuously transports the second web W2, and is in contact with the surface of the second roller 12 via the first web W1, the elastic member F, and the second web W2 at a contact point O (predetermined position). Thereafter, the following may also be possible: an additional roller and the pad $9_i$ sandwich the first web W1, the elastic member F, and the second web W2 placed on the pad $9_i$, whereby the contact therebetween is enhanced.

The elastic member F is cut after being interposed between the first web W1 and the second web W2. The elastic member F is fixed between the webs W1 and W2, so that the elastic member F shrinks less, compared with the case where the elastic member F is placed on one web.

The rotation apparatus 1 receives the second web W2 at a circumferential velocity V11 at a receiving position RP. At a point "A" where the pad $9_i$ receives the second web W2, the circumferential velocity of the pad is V11. FIG. 5A is a side view showing the enlarged vicinity of the point "A" of FIG. 1. During a period from a time when at least a part of the pad $9_{i+1}$ shown in FIG. 5A receives the second web W2 to a time when at least a part of the pad $9_i$ adjacent to the pad $9_{i+1}$ receives the second web W2, the pad $9_{i+1}$ moves at a substantially constant circumferential velocity V11. The reason for this is to prevent the second web W2 from being damaged.

Each pad $9_i$ of the rotation apparatus 1 is rotated at the receiving position RP at the circumferential velocity V11, and decelerates to a circumferential velocity V21 before reaching the contact point O (where the distance between the pad $9_i$ and the pad $9_{i+1}$ becomes minimum). Therefore, the interval between the pad $9_i$ and the pad $9_{i+1}$ becomes narrow before the pad $9_i$ moves from the receiving position RP to the contact point O. This causes the second web W2 to become loose between the pad $9_i$ and the pad $9_{i+1}$, whereby a loose portion Wa is formed.

The pad $9_i$ comes into contact with the second roller 12 via the second web W2 and the like at the circumferential velocity V21 (V11>V21) at the contact point O shown in FIG. 1. The first web W1 is transferred from the second roller 12 at the circumferential velocity V2. The circumferential velocity V21 of the pad $9_i$ is set at a substantially constant velocity equal to or close to the circumferential velocity V2 of the second roller 12. That is, while at least the pad $9_i$ is in contact with the second roller 12 via the second web and the like or at least the pad $9_i$ places the first web W1 on the second web W2, the pad $9_i$ moves at the substantially constant circumferential velocity V21 substantially equal to V2. In other words, during a period from a time when the second web W2 on the pad $9_i$ starts receiving the first web W1 to a time when the second web W2 finishes receiving it, the pad $9_i$ moves the constant circumferential velocity V21 ($\approx$V2). The difference in velocity prevents the first web W1 and the second web W2 from being shifted from each other, and exactly places the first web W1 at a predetermined position of the second web W2.

The circumferential velocity of the pad $9_{i+1}$, becomes V31 at a point B where the pad $9_{i+1}$ releases the second web W2. FIG. 5B is a side view showing the enlarged vicinity of the point B. The pad $9_i$ moves at a substantially constant circumferential velocity V31 at least during a period from a time slightly before the pad $9_{i+1}$ adjacent to the pad $9_i$ releases the second web W2 to a time when the pad $9_i$ releases the second web W2 (FIG. 5B). The reason for this is to minimize the fluctuation in velocity of the released second web W2. For example, in the case where the circumferential velocity of an embossing roller 5 is V3, the circumferential velocity V31 becomes substantially equal to V3.

When or after the circumferential velocity of the pad $9_i$ becomes maximum in the vicinity of the point A in FIG. 5A, the pad $9_i$ receives the second web W2. If the pad $9_i$ receives the second web W2 before the circumferential velocity of the pad $9_i$ becomes maximum, the interval between adjacent pads is increased, which may damage the second web W2. As the operation of the pad $9_i$, the pad $9_i$ may move at a maximum circumferential velocity, for example, during a period from the point B to the point A. In this case, a region from the point B to the point A can be dealt with as one region. That is, in the present embodiment, the circumferential velocity of the pad may become substantially constant at least at two points.

It is preferable that the apparatus is provided with a directing part so that the loose portion Wa in FIG. 1 becomes loose exactly toward the center of the rotation apparatus 1.

The directing part may be, for example, a mechanism for jetting air or a mechanism for pushing the loose portion Wa of the web toward the center of the rotation apparatus 1. Alternatively, the directing part may be a mechanism for sucking the web W toward the center of the rotation apparatus 1 by vacuum suction. In the case where the directing part is a mechanism for jetting air, one or a plurality of directing parts may be provided. Furthermore, in the case where the directing part is a mechanism for pushing the loose portion Wa, one or a plurality of directing parts may be provided. By providing a plurality of directing parts, the loose portion Wa can be bent exactly toward the center of the rotation apparatus 1. In the present embodiment, the loose portion Wa may have a shape dented toward the center of the rotation apparatus 1 due to the weight of the second web W2.

Next, a folding operation will be described. When the second web W2 is sucked to be held on the surface of the pad $9_1$ at the receiving position RP, the second web W2 is transported along the pad $9_1$ of the rotation apparatus 1. When the pad $9_1$ is rotated from the receiving position RP to the contact point O, the interval between the pads $9_i$ is decreased. Because of this, the loose portion Wa is formed in the second web W2. Furthermore, the loose portion Wa is folded into two to form a folded portion Wb.

The rotation apparatus for conducting the above-mentioned "folding" is not limited to the rotation apparatus 1. For example, an apparatus described in Japanese Patent Application No. 2001-545183 A may be used. The present invention is intended to place an elastic member intermittently on a web. Therefore, the second web W2 is not necessarily folded completely. Furthermore, depending upon the shape of the pad $9_i$, the second web W2 may have a loop shape.

Figure 2:
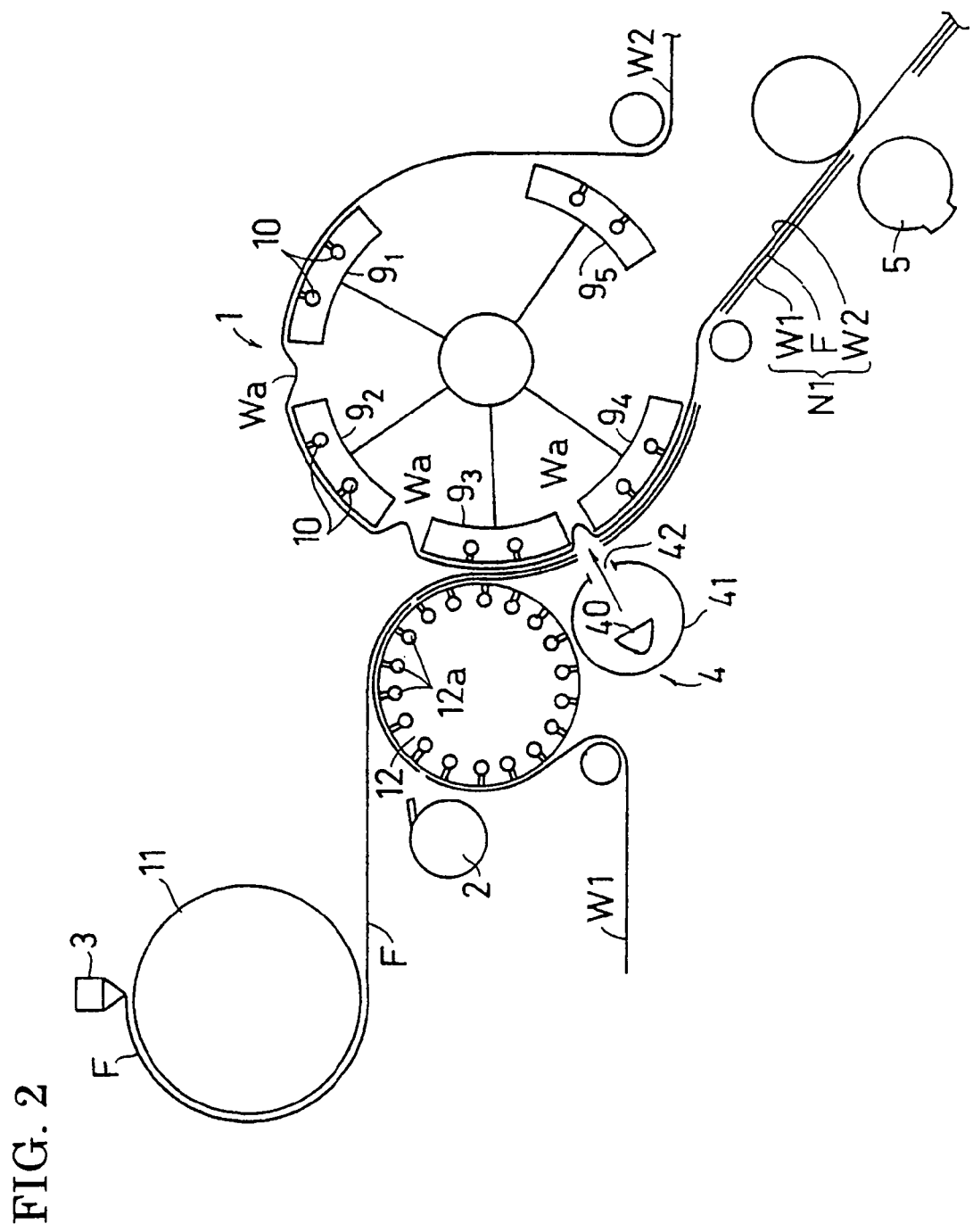
FIG. 2 is a side layout view illustrating the steps of cutting an elastic member in the apparatus shown in FIG. 1.

The folded second web W2 is attached to be stacked on the first web W1 at non-folded portions Wc before and after the folded portion Wb. That is, the elastic member F is not cut until the elastic member F is placed and fixed between the first web W1 and the second web W2. Therefore, the stretched elastic member F hardly shrinks on the second web W2. When the second web W2 is stacked on the first web W1, the first web W1 is not placed on the folded portion Wb folded between the pads $9_i$ and $9_{i+1}$ adjacent to each other in the vicinity of the contact point O. When the interval between the pads $9_i$ and $9_{i+1}$ is increased as shown in FIG. 2, only the elastic member F is exposed as shown in FIG. 3A.

As shown in FIG. 1, during β from a time when the first web W1 is attached to the second web W2 to a time when the first web W1 is received, suction of air through the suction holes 12a of the second roller 12 may be stopped or air may be discharged through the suction holes 12a. The purpose of this is to attach the first web W1 to the second web W2 smoothly.

Figure 3A:
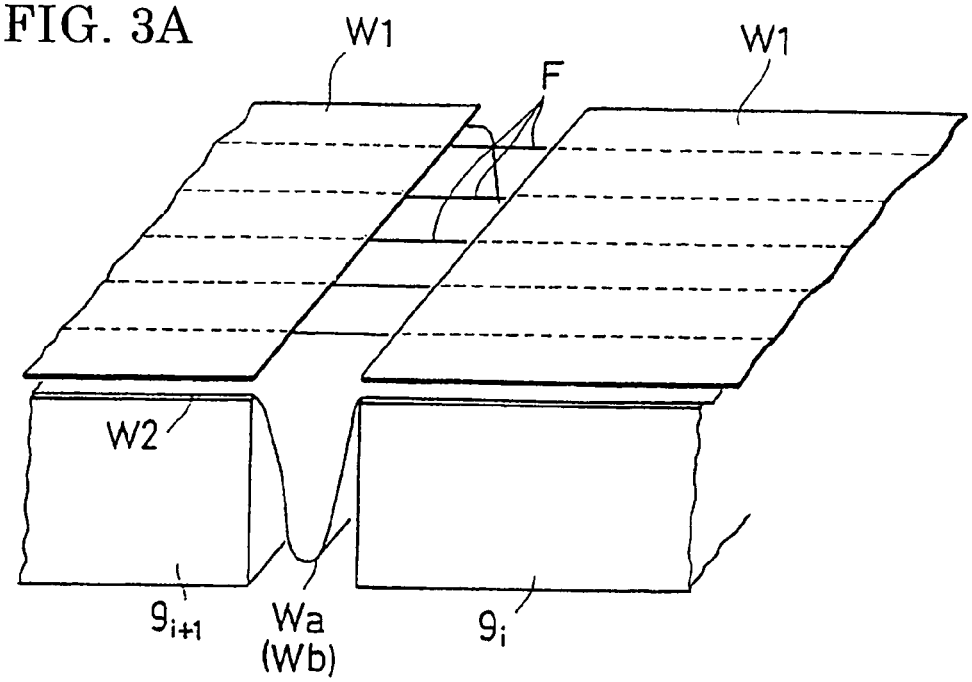
FIG. 3A is a perspective view of a stack in a state before the elastic member is cut.

The exposed elastic member F in FIG. 3A is cut with a cutter. In the case where the elastic member F can be cut with a light cutter, a light cutter 4 shown in FIG. 2 is used. The light cutter 4 has a rotatable cover, and a slit 42 is formed at a part of the cover. The cover 41 with the slit 42 is rotated, whereby infrared rays are radiated intermittently from a light source 40 to the elastic member F to cut it at a predetermined pitch. When the elastic member F is cut with the light cutter 4, there is no possibility that the webs W1 and W2 are damaged by heat from the light cutter 4, since the elastic member F is away from the loose portion Wa. The elastic member F may be cut with a pressure, heat, UV-rays, a laser or at least two of them. Furthermore, the elastic member F may be cut with an ultrasonic wave.

Figure 11A:
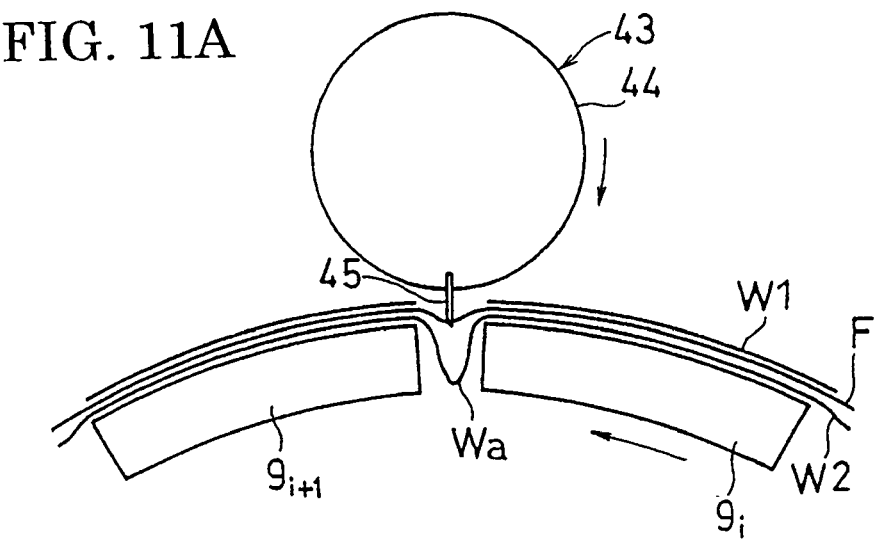
FIGS. 11A to 11C show an example of cutting the elastic member with a cutting machine.
Figure 11B:
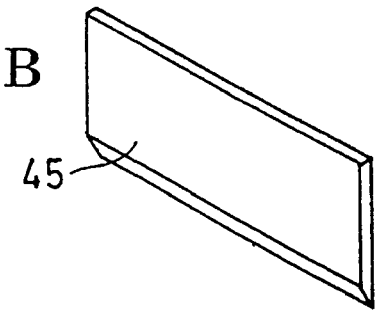
Figure 11C:
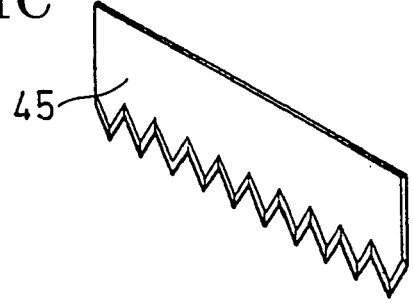

Hereinafter, an example of cutting the elastic member F with a cutter will be described. FIG. 11A is a view showing a cutting machine 43 that is an example of a cutter. The cutting machine 43 has a rotatable roller 44 and at least one of blade 45 placed at the roller 44. The distance between the rotation center of the roller 44 and the center of the rotation apparatus 1 is hardly changed. The blade 45 can cut the elastic member F positioned on the loose portion Wa between the pads $9_i$ and the pad $9_{i+1}$, when the roller 44 is rotated. The rotation of the roller 44 is changed in accordance with the rotation of at least one of the pad $9_i$ and the pad $9_{i+1}$. The blade (s) 45 may have a linear shape (FIG. 11B) or may be in a jagged shape (FIG. 11C). Furthermore, the blade 45 may be reciprocated in the direction of the rotation axis.

Figure 11D:
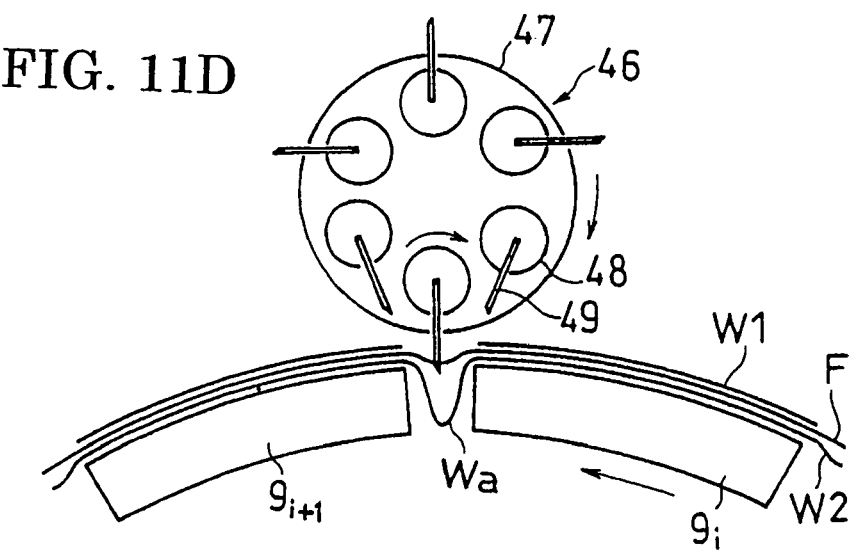
FIG. 11D shows another cutting machine.

FIG. 11D shows another cutting machine 46. The cutting machine 46 includes a rotatable large roller 47, a rotatable small roller 48 attached to the large roller 47, and a blade 49 placed at the small roller 48. The blade 49 of the cutting machine 46 can cut the elastic member F positioned on the loose portion Wa between the pad $9_i$ and the pad $9_{i+1}$, when the large roller 47 and the small roller 48 are rotated. The rotations of the large roller 47 and the small roller 48 are changed in accordance with the rotation of at least one of the pad $9_i$ and the pad $9_{i+1}$. As shown in FIG. 11D, when the blade 49 reaches the bottom dead point, the tip end of the blade 49 is preferably directed to the center of the rotation apparatus 1. Furthermore, in the same way as in the blade 45, the blade 49 may have a shape as shown in FIG. 11B or 11C, and may be reciprocated in the direction of the rotation axis of the large roller 47 or the small roller 48.

The small roller 48 of the cutting machine 46 may have a plurality of blades 49 as shown in FIG. 11E. The blades 49 may be reciprocated in the direction of the rotation axis to cut the elastic member.

The rotation apparatus 1 may be provided with scissors instead of the cutting machine. After the second web W2 is stacked on the first web W1, and the interval between the pad 9$_i$ and the pad 9$_{i+1}$ is slightly increased, the scissors may enter between the pad 9$_i$ and the pad 9$_{i+1}$ to cut the elastic member stretched between the pad 9$_i$ and the pad 9$_{i+1}$. The scissors may enter between the pad 9$_i$ and the pad 9$_{i+1}$ in accordance with the rotation of at least one of the pad 9$_i$ and the pad 9$_{i+1}$. In order for the scissors to perform such an operation, at least one of a cam mechanism and a link mechanism may be used.

In FIG. 1, the circumferential velocity of the pad 9$_3$ becomes a velocity V31 (V31>V21) at a releasing position SP where the pad 9$_3$ releases the second web W2. Therefore, the interval between the pads 9$_3$ and 9$_4$ is increased from the contact point O to the releasing position SP. Therefore, the tension stress and elongation of the elastic member F are increased from the contact point O to the releasing position SP. When the elastic member F is cut with the light cutter 4 in this state, cutting becomes easy. At the releasing position SP, a stack N1 in FIG. 3B, in which the webs W1 and W2 and the elastic member F are stacked, is in the state before the folded portion Wb is folded.

Herein, during α from the releasing position SP to the receiving position RP, suction through the suction holes 10 may be stopped, and air may be discharged through the suction holes 10. The purpose of this is to smoothly transfer the stack N1 in a downstream direction.

Figure 3B:
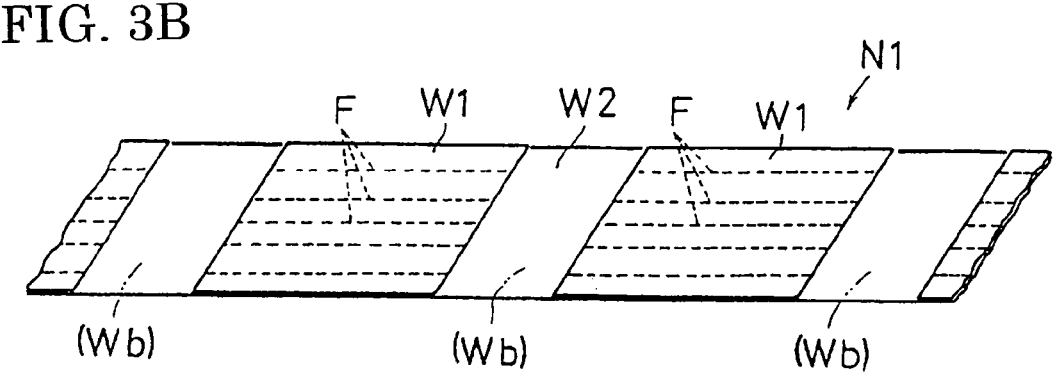
FIG. 3B is a perspective view of a stack in a state after the elastic member is cut.
Figure 4A:
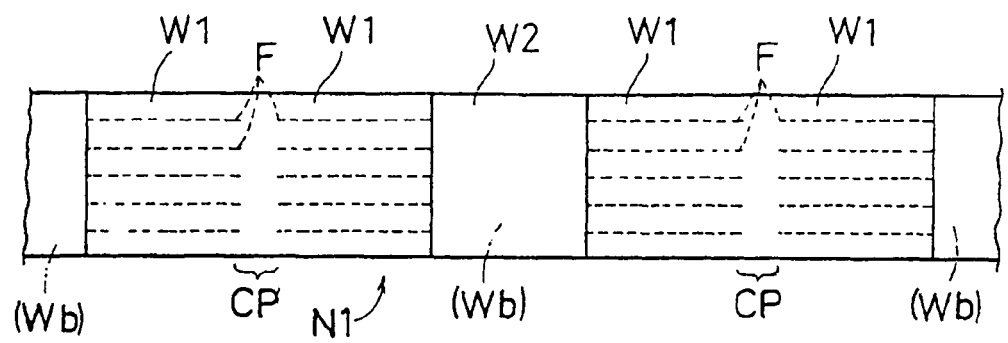
FIG. 4A is a front view showing the stack in which the elastic member interposed between webs is cut.

As shown in FIG. 1, an embossing roller 5 may be provided downstream from the releasing position SP. The stack N1 in FIG. 3B is sent to the embossing roller 5. A plurality of convex portions 51 are arranged on the embossing roller 5, and at least the elastic member F of the stack N1 is cut with the convex portions 51. Because of this, as shown in FIG. 4A, the stack N1 is obtained in which the shrinking force of a part of the elastic member F interposed between the first and second webs W1 and W2 is suppressed. An adhesive is not basically applied to a portion CP where the shrinking force of the elastic member F is suppressed by the embossing roller 5. The reason for this is to protect the shrinking of the elastic member F. However, in order to control the shrinking of the elastic member F, some adhesive weaker than usual may be applied.

Figure 4B:
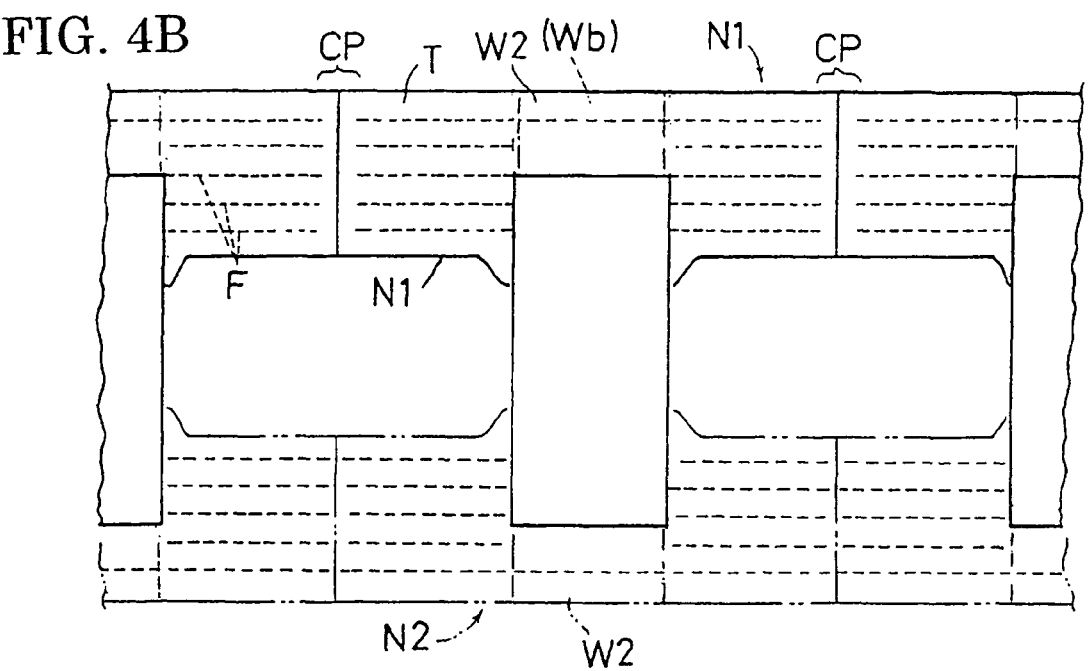
FIG. 4B is a front view showing a wearing article.

A portion represented by a solid line in FIG. 4B shows an example of a disposable diaper produced by the production method of the present invention. In the stack N1, at least a part of an absorber C is fixed at the portion Wb of the stack N1 where the elastic member F is not placed. The other end of the absorber C is connected to another stack N2 represented by a broken line. The absorber C is folded into two, and the portion CP of the stack N1 comes into contact with a corresponding portion of another stack N2, whereby continuous disposable diapers can be produced. Another stack N2 may have the same configuration as that of the stack N1. Furthermore, in the case where the absorber C is folded into two, and the portion CP of the stack N1 comes into contact with the corresponding portion of another stack N2, whereby the stacks N1 and N2 are stretched in a flow direction, even if the elastic member F is placed at the portion CP, the above connection can be conducted.

Figure 12:
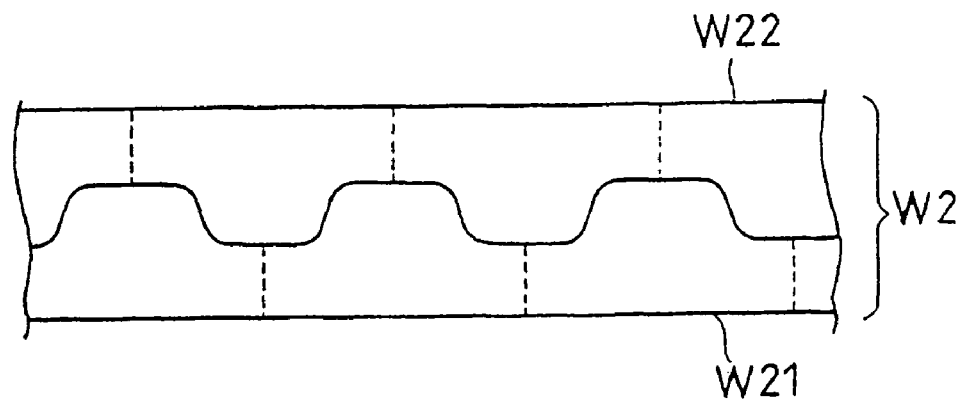
FIG. 12 shows diapers obtained by cutting the elastic member so that a trim is not generated, and shifting the phase of one web thus cut by substantially ½ from the other web.

Furthermore, the following may also be possible: when the elastic member F is cut so that a trim is not generated as shown in FIG. 12, and the phase of one web thus cut is shifted by substantially ½ from the other web, whereby the web W2 shown in FIG. 4B is formed. As a method for shifting a phase, one web may be allowed to pass through a dummy roller to cause a delay from the other web.

Embodiment 2

Figure 6:
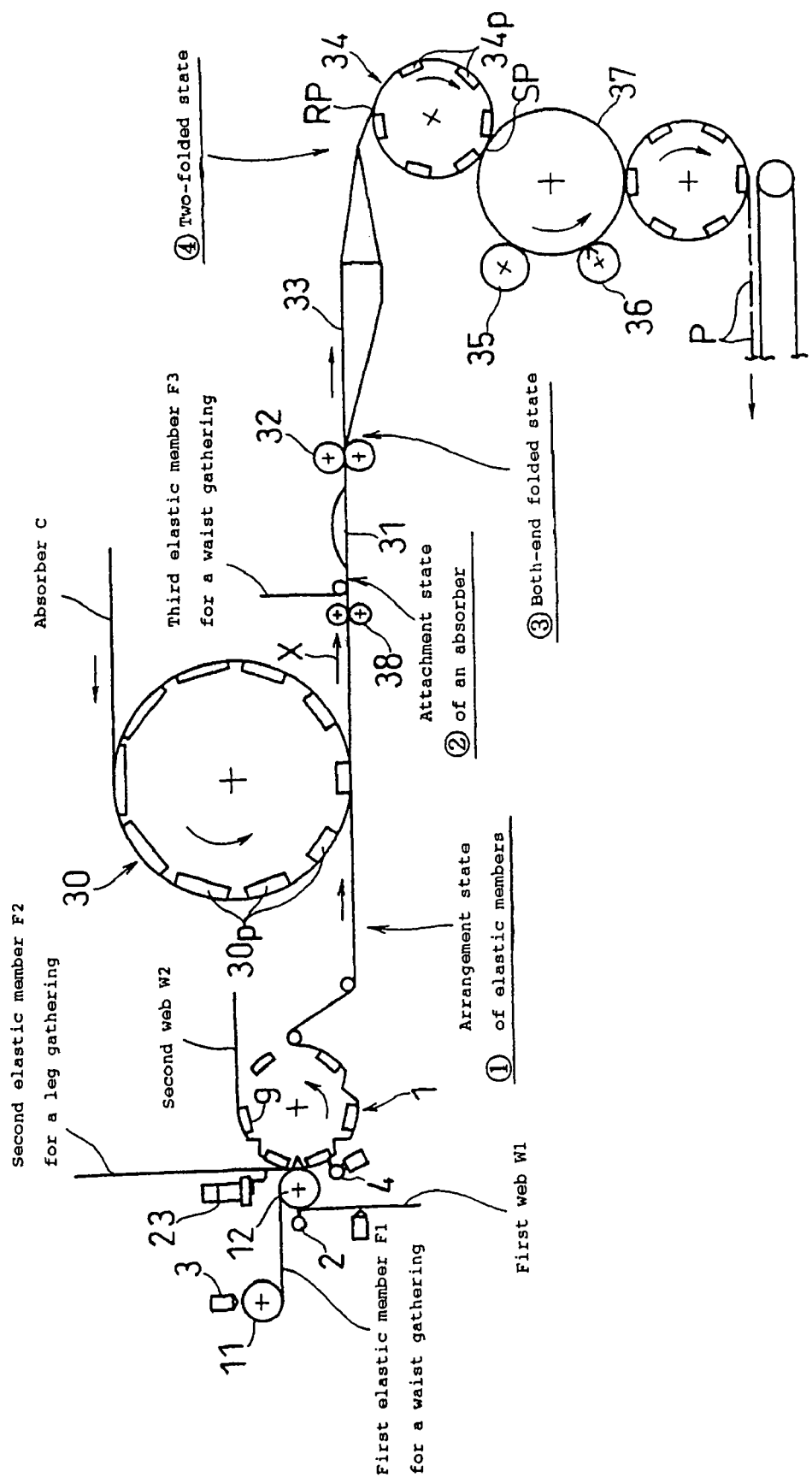
FIG. 6 is a side layout view showing an apparatus for producing a wearing article of Embodiment 2 according to the present invention.
Figure 9A:
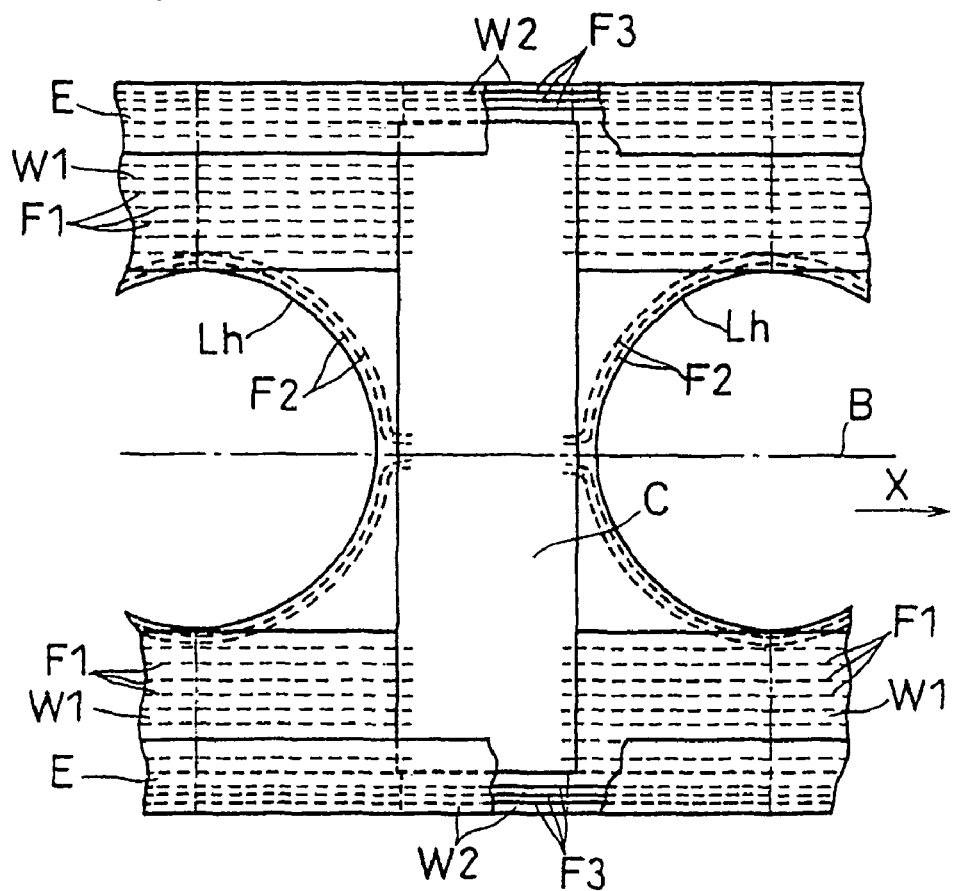
FIG. 9A shows webs whose both edges are bent.

Next, Embodiment 2 will be described. A production apparatus shown in FIG. 6 is capable of placing at least three kinds of elastic members F1 to F3 for a leg gathering on a wearing article, as shown in FIG. 9A.

Figure 7:
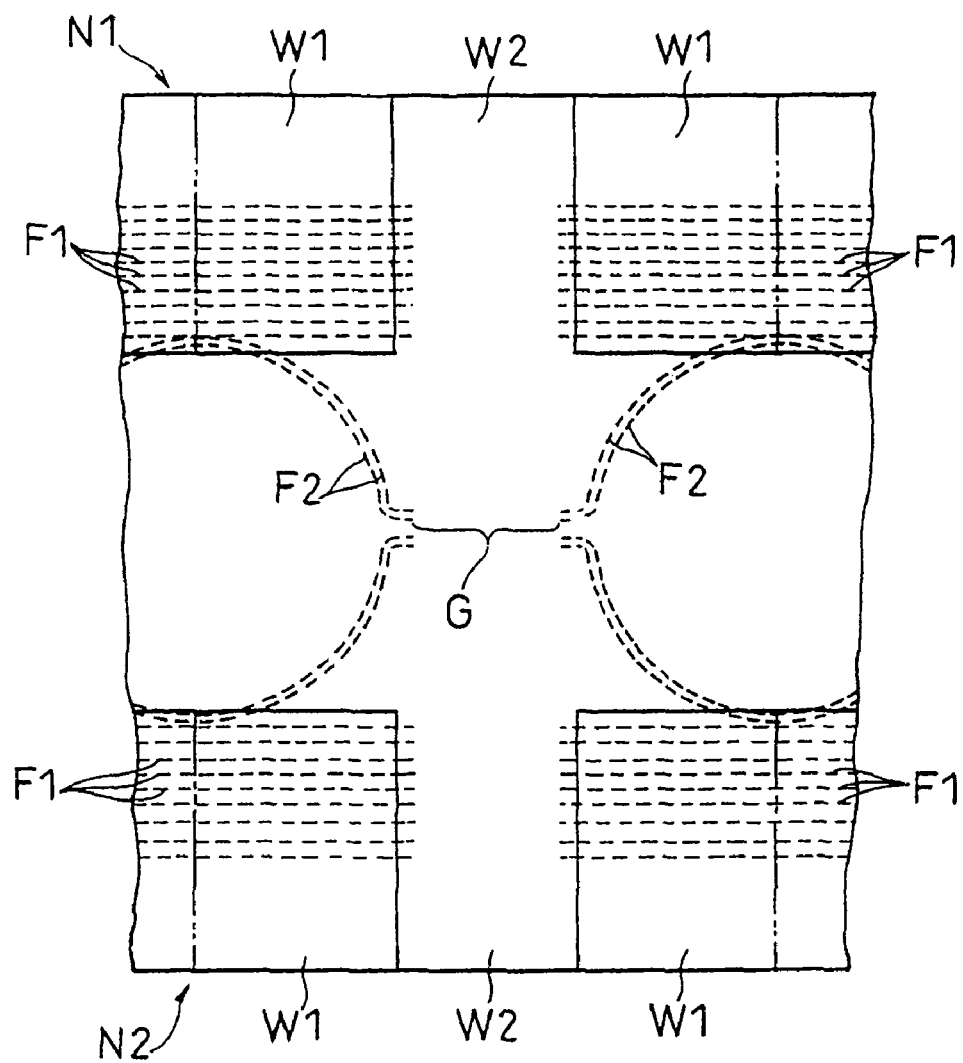
FIG. 7 is a front view showing webs in a state where the elastic member is placed.

(1) Arrangement State of Elastic Members:

First, as shown in FIG. 7, the configuration and operation of the present apparatus for obtaining an arrangement state of elastic members, in which first and second elastic members F1 and F2 are placed on webs W1 and W2, will be briefly described.

The present apparatus includes a first roller 11 for placing a first elastic member 1 for a waist gathering and a guide unit 23 for placing a second elastic member 2 for a leg gathering. The guide unit 23 is capable of arranging the second elastic member F2 for a leg gathering in a curved shape or a linear shape by being reciprocated in the axis direction of a second roller 12 with, for example, a cam or a servo motor. U.S. patent application Ser. No. 10/095,959 discloses an example of the guide unit 23. The second elastic member F2 may be cut mechanically with scissors, a blade, or the like provided at the roller. FIGS. 11A to 11D show examples of a cutter. The first elastic member F1 may not be a thermoplastic elastic member. In this case, the first elastic member F1 can be cut with scissors, a blade, or the like in the same way as in the second elastic member F2. Furthermore, the first and second elastic members F1 and F2 may be cut with the same scissors, blade, or the like. In the steps until here in Embodiment 2, the other configuration is the same as that of Embodiment 1. Like parts are denoted with like reference numerals, and the detailed description and drawings are omitted here.

After being interposed and fixed between the first and second webs W1 and W2, the first and second elastic members F1 and F2 are cut to be arranged as shown in FIG. 7.

In some disposable wearing articles, an elastic member for a leg gathering is placed on a crotch portion. Therefore, such a portion contrasts to cause an unsatisfactory feeling during wearing. In order to avoid this, the elastic member on the crotch portion is cut so as to shrink, whereby the elastic member on the crotch portion can be made short to some degree. However, it is impossible to completely eliminate the elastic member on the crotch portion, so that an unsatisfactory feeling may still remain.

Figure 10A:
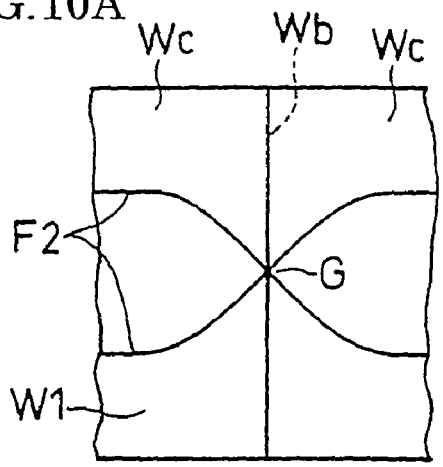
FIGS. 10A to 10F are front views illustrating a method for placing a second elastic member.
Figure 10B:
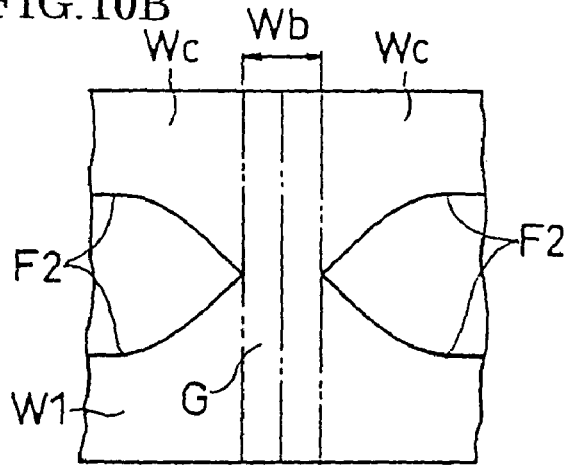
Figure 10C:
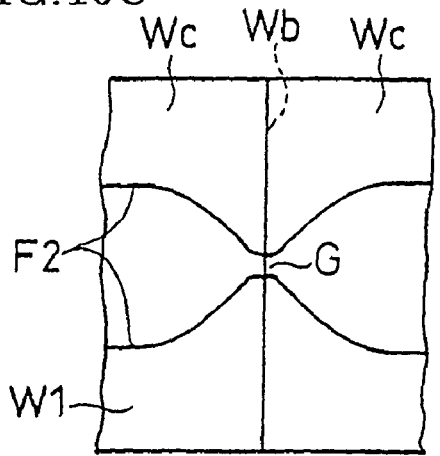
Figure 10D:
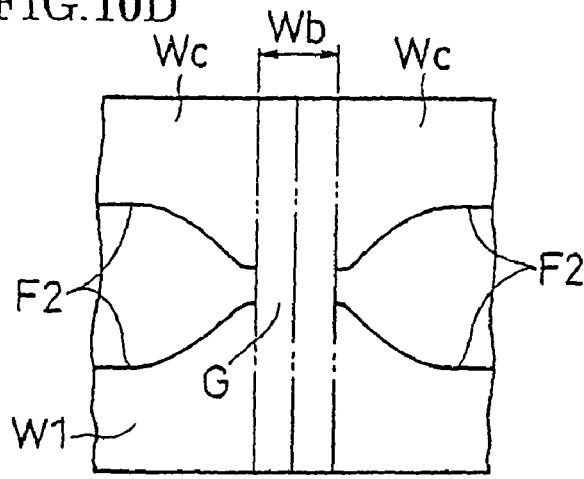
Figure 10E:
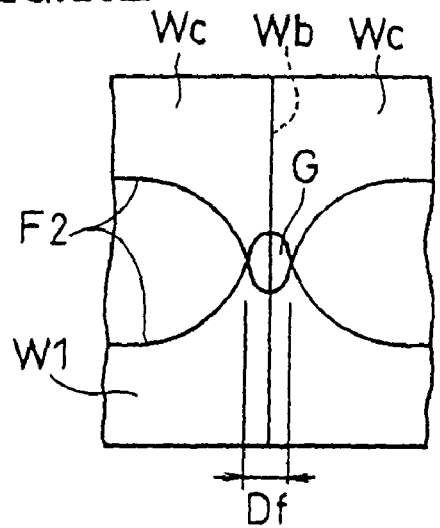
Figure 10F:
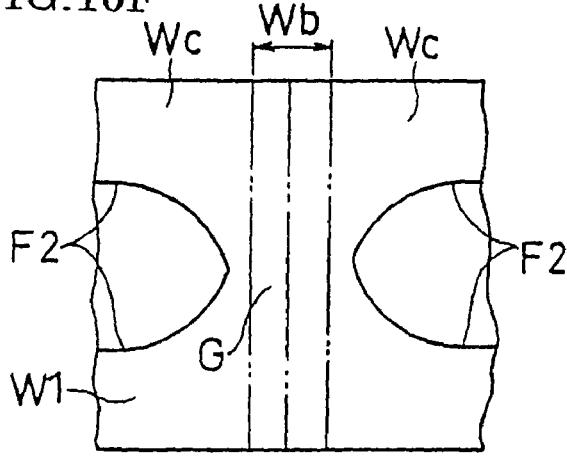

In contrast, when the second elastic member F2 for a leg gathering is placed as shown in FIGS. 10A, 10C, and 10E, the second elastic member F2 can be eliminated from the crotch portion G. FIGS. 10A, 10C, and 10E show the second elastic member F2 interposed between the first web W1 and the second web W2 on adjacent pads 9, wherein a part of the web W2 is interposed between the adjacent pads 9.

For example, as shown in FIGS. 10A and 10c, a folded portion Wb is formed on the crotch portion G of the first web W1, and the second elastic member F2 is placed on non-folded portions Wc. Thereafter, the second elastic member F2 striding across the adjacent pads 9 is cut. As a result, the second elastic member F2 is not placed on the crotch portion G, as shown in FIGS. 10B and 10D.

Furthermore, as shown in FIG. 10e, when a non-coated portion Df with no adhesive applied there to is provided in the non-folded portion Wc adjacent to the vicinity of the folded portion Wb, after the second elastic member F2 is cut, a portion of the second elastic member F2 that is not sufficiently attached to the non-folded portion Wc shrinks (FIG.

10F). Full-circle pants may be produced by such adjustment of an adhesive. Some adhesive may be applied to the non-coated portion Df. In this case, the second elastic member F2 shrinks slowly without being fixed to the non-folded portion Wc, and finally, the second elastic member F2 can be eliminated from the crotch portion G.

The adhesive only needs to be applied to a portion where the second elastic member F2 is placed. As a coating method, an adhesive may be applied in an annual shape to at least one of the first and second webs W1 and W2 with a coater or the like. Furthermore, guns with a plurality of valves are placed in a direction across the first web W1 so that opening/closing of the valve may be controlled by the flow speed of at least one of the first web W1 and the second web W2 and the coating shape. In the case of using such guns, an adhesive can be applied in arbitrary regions partitioned in a matrix.

(2) Attachment State of an Absorber:

An absorber C is arranged and attached to the webs W1 and W2 in the above-mentioned arrangement state of the elastic members by a turn apparatus 30. Thereafter, a third elastic member F3 for a waist gathering is placed to form an attachment state of an absorber as shown in FIG. 8.

The turn apparatus 30 is provided with a plurality of suction pads 30p around a drum (not shown). The suction pads 30p are rotated in an arrow direction while changing the posture of the absorber C by 90° by turning. As the turn apparatus 30, for example, an apparatus as disclosed by International Publication No. WO 01/44086 or U.S. Patent Application Publication No. US 2002/0103468 may be used, as is described in more detail below.

Figure 8:
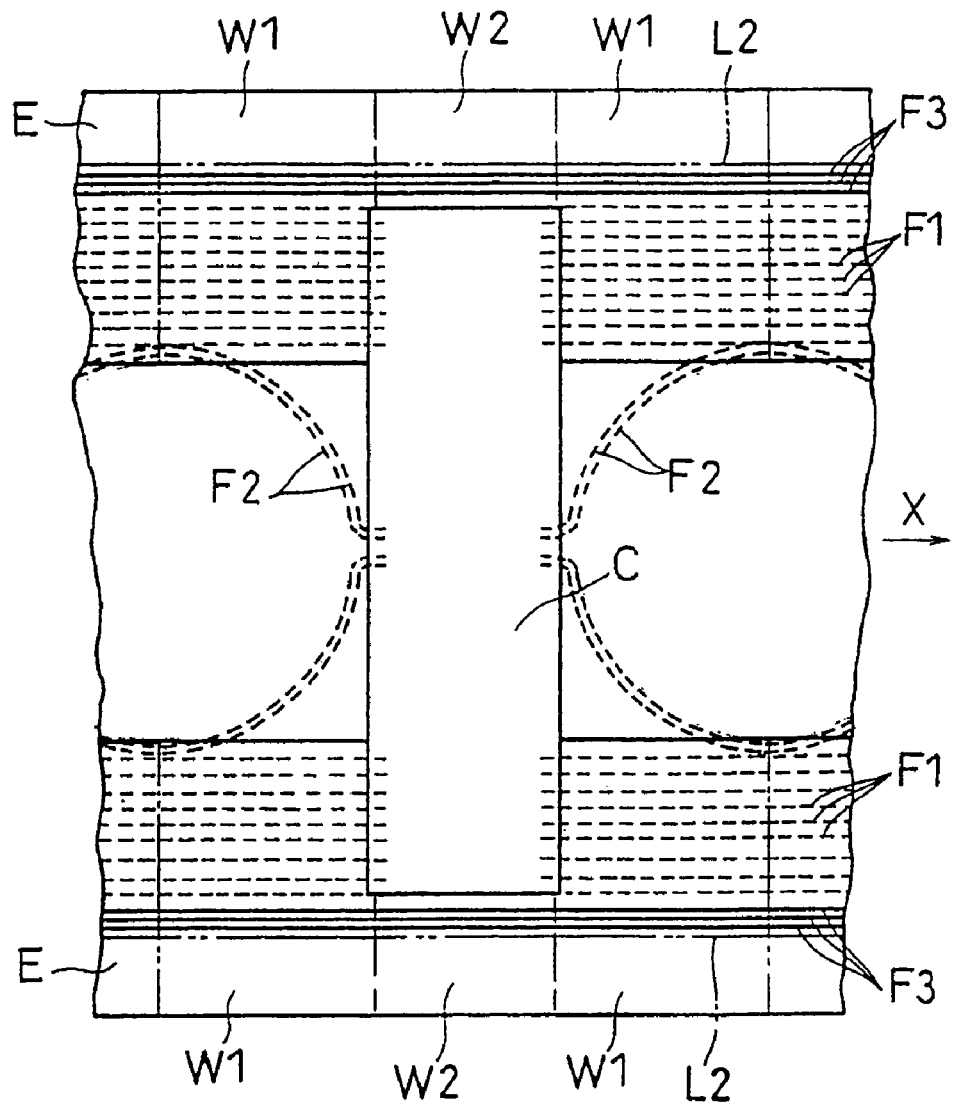
FIG. 8 is a front view showing webs in a state where an absorber is attached.

(3) Both-Edge Folded State:

Thereafter, the webs W1 and W2 with the absorber attached thereto have their folding portions E on both edges folded inward at a position of two-dot dash lines $L_2$ shown in FIG. 8 by a folding apparatus 31. After both edges of the webs W1 and W2 are folded, a leg hole Lh is cut out with a leg hole cutter 32 (FIG. 6), whereby a both-edge folded state shown in FIG. 9A is formed. The leg hole cutter 32 may be placed upstream from the turn apparatus 30. In such a configuration, it also becomes possible to produce a disposable wearing article in which a part of the absorber C extends out to the leg hole Lh portion.

Figure 9B:
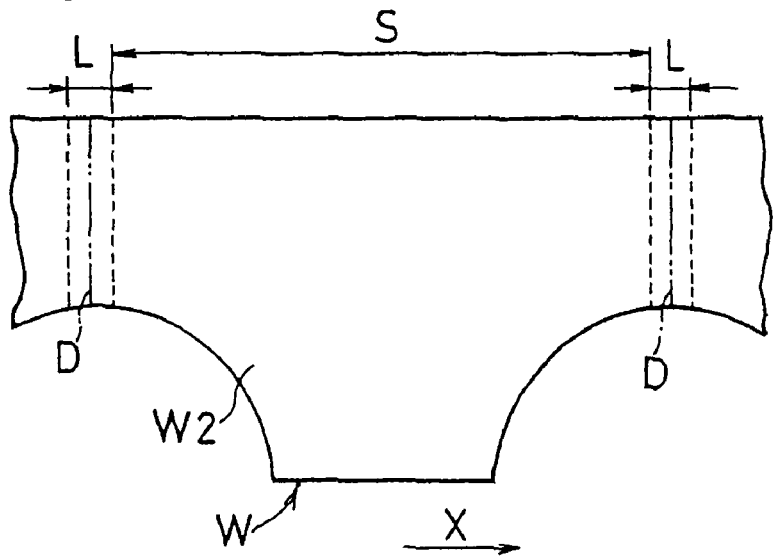
FIG. 9B shows webs folded into two.

(4) Two-Folded State:

After folding, the webs W1 and W2 are folded into two at a folding line B by a two-folding apparatus 33, whereby the webs W1 and W2 are folded into two as shown in FIG. 9B. As the two-folding apparatus 33, for example, an apparatus described in U.S. Pat. No. 3,828,367, U.S. Pat. No. 5,711,832, or U.S. patent application Ser. No. 10/147,644 may be used.

Thereafter, the webs W1 and W2 folded into two have both edges L sealed (e.g., heat-sealed or sonic-sealed), as shown in FIG. 9B. Thereafter, a cutting portion D represented by a two-dot dash line is cut to form an individual disposable wearing article, e.g., pants P.

The present apparatus may form pants P from the webs W1 and W2 (hereinafter, referred to as a "stacked web W") folded into two, using a decelerating drum 34, a main drum 37, a seal roller 35, and a cutter roller 36.

Decelerating Drum 34:

As described above, although the web W has an elastic member, the web W is moved in a stretched state so that placement of an absorber at a predetermined position, formation of a leg hole, and other processing can be performed easily. However, in order to seal the web W and cut a seal portion, the position of the edge L only needs to be determined. This is because the state of the other portions of the web W does not influence a sealing step and a cutting step.

Furthermore, in the sealing step, it is preferable that a flow speed of the web W is lower so as to obtain a sufficient time for melting a part of the web W and the like. The decelerating drum can decrease the flow speed of the web W so as to obtain a sufficient time for melting the part of the web W and the like. As the decelerating drum 34, an apparatus described in JP 63-317576 A, International Publication No. W0 01/44086, or U.S. Patent Application Publication No. 2002/0103468 may be used.

The decelerating drum 34 is provided with a plurality of pads 34p rotating in a transport direction of the stacked web W around a drum (not shown). The decelerating drum 34 receives at least an edge L at a receiving position RP from the two-folding apparatus 33 placed upstream therefrom, and holds it. The other portions of the web W are positioned between adjacent pads 34p. The edge L is transported to a releasing position SP, and thereafter, the edge L is supplied to the main drum 37 placed downstream there from at the releasing position SP. While the pad 34p moves from the receiving position RP to the releasing position SP, the interval between the adjacent pads 34p is changed to be narrow.

The pad 34p is capable of receiving the edge L in a stretched state at the receiving position RP, and keeping holding the edge L shown in FIG. 9B. For example, the edge L may be held by sucking the edge L, pressing the edge L with a hook, or fixing the edge L with a pin placed at the pad 34p. On the other hand, the interval between the adjacent pads 34p, which has been increased at the receiving position RP, is decreased before the releasing position SP, and a shrinking portion S excluding the edge L shrinks in a transport direction X. In order to allow the edge L to be exactly held, the shrinking force of the elastic member positioned at the edge L may be weakened by an embossing roller 38. For example, the embossing roller 38 can cut the elastic member to a predetermined length or change the elastic configuration of the elastic member by using at least one of heat and pressure. As the embossing roller 38, for example, an apparatus described in U.S. Patent Application Publication No. 2002/0103468 may be used. The embossing roller 38 is placed in a region from the rotation apparatus 1 to the two-folding apparatus 33.

Main Drum 37:

The main drum 37 receives the web W in a mixed state where the stretched edge L and the shrinking portion S that has shrunk are present alternately from the decelerating drum 34. The main drum 37 transports the web W in such a mixed state. In order to keep the mixed state, the main drum 37 may be provided with, for example, a plurality of suction holes to suck air through the suction holes so as to suck the web W.

Seal Roller 35:

The seal roller 35 can conduct heat-sealing by heating and pressing the edge L (FIG. 9B) of the web W. More specifically, the web W is pressed by being interposed between the seal roller 35 and the main drum 37, and heated by the seal roller 35. The seal roller 35 may be provided with, for example, a heater so as to heat-seal the edge L. Furthermore, the seal roller 35 may have a horn to conduct sonic-sealing. The web W subjected to the above-mentioned heat-sealing is cut to individual pants P by a cutter roller 36 placed downstream therefrom.

Formation Operation of Pants P:

Next, an operation of forming pants P from the stacked web W will be described. The decelerating drum 34 continuously receives the web W onto each pad 34p under the condition that the web W is stretched in a flow direction. Herein, the pad 34p holds the edge L (FIG. 9B) of the web W in a stretched state.

After receiving the web W, the pad 34p having received the web W has its circumferential velocity decreased, whereby the interval between the adjacent pads 34p becomes narrow. Therefore, a portion S other than the edge L of the web W shown in FIG. 9B shrinks in a transport direction X to form the shrinking portion S. On the other hand, the edge L is held in a stretched state.

Thereafter, the main drum 37 receives the web W from the decelerating drum 34. At this time, the main drum 37 receives the web W in a mixed state where the edge L in a stretched state and the shrinking portion S that has shrunk are present alternately. The main drum 37 transports the web W in a downstream direction while keeping the mixed state. During transportation by the main drum 37, the seal roller 35 presses and heats the edge L of the web W on the main drum 37. Herein, a part of the web W shrinks, so that the transport velocity of the web becomes low. Sealing can be conducted exactly, as the transport velocity of the web W is low.

Thereafter, the web W is cut to individual pieces with a cutter roller 36 to form pants P.

As described above, according to the present invention, after being interposed and fixed between a first web and a second web, an elastic member is cut. Therefore, the stretched elastic member hardly shrinks on the second web, whereby an expected gathering is obtained.

Furthermore, according to the present invention, the elastic member is cut between adjacent first webs. Therefore, the second web and an absorber do not become stiff between the first webs.

Furthermore, a plurality of first webs are placed on a second web under the condition where they are away from each other. Therefore, the first web is not stacked on a portion where a gathering of the elastic member is not formed, so that such a portion becomes thin and allows air to pass therethrough. As a result, a user wearing such an article is not likely to feel stuffy.

Furthermore, the elastic member is cut between the first webs and at a loose portion of the second web. Therefore, only the elastic member can be cut without damaging the web.

If a pad that makes the second web loose is allowed to transport the second web at a substantially constant velocity during a predetermined period from a time when the pad starts receiving the first web to a time when the pad finishes receiving it, the first web can be transferred to a predetermined position of the second web exactly.

Furthermore, if the elastic member is cut under the condition that the tension stress of the elastic member is increased, the elastic member can be cut easily with infrared rays or the like.

Furthermore, while the web is transported under the condition that an edge (where the web is stretched) and a shrinking portion (where the web shrinks) are present alternately in a transport direction, a heating time for heating the edge becomes long. Therefore, the transport velocity of the web can be increased without impairing the exactness of heat-sealing.

Referring now to FIGS. 13A-28, further detail regarding the rotation apparatus or device will be described as originally set forth in U.S. Patent Application Publication No. US 2002/0103468.

Figure 13B:
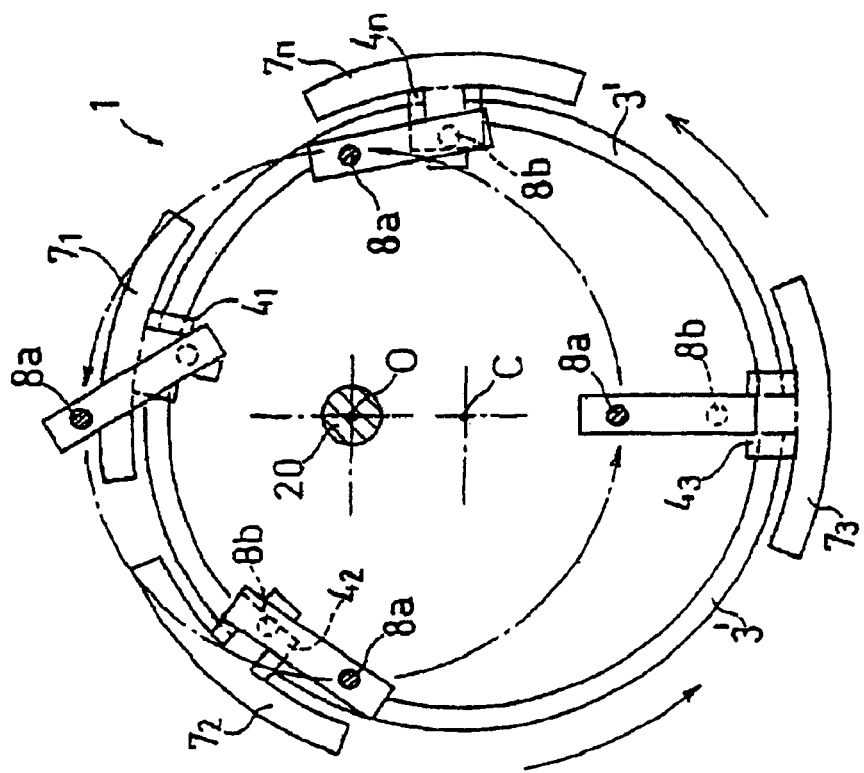
FIG. 13B is a side view illustrating the first embodiment of the rotation device of the present invention.
Figure 13A:
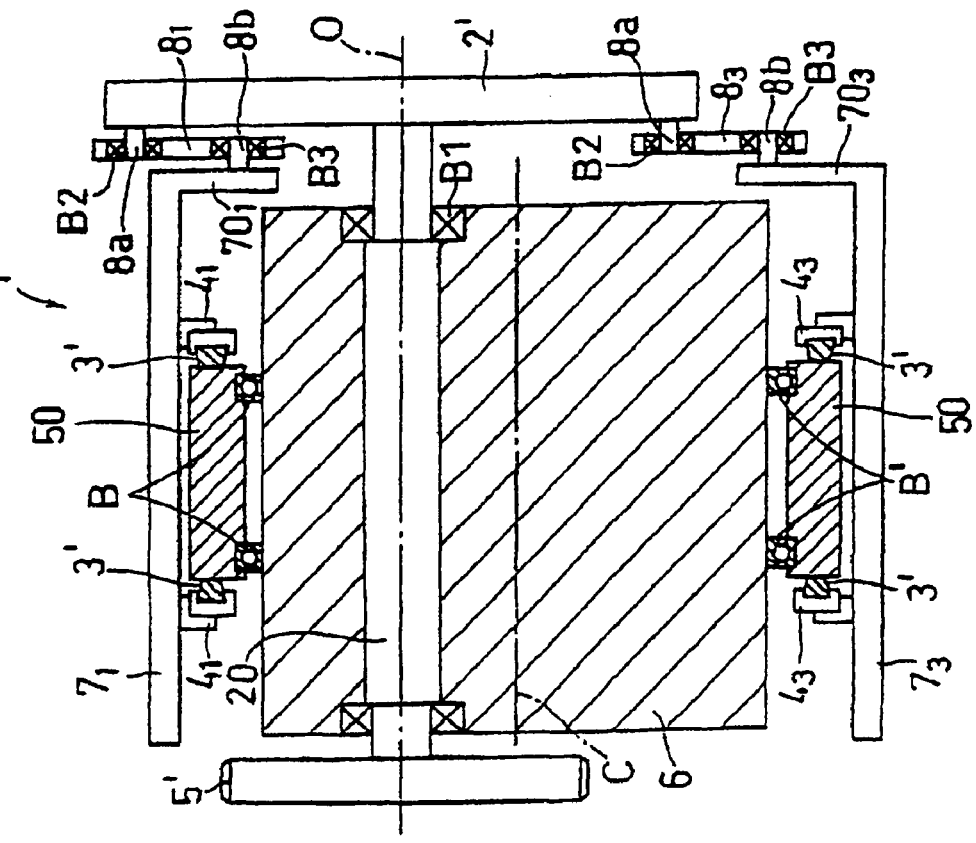
FIG. 13A is a schematic cross-sectional view illustrating a first embodiment of the rotation device of the present invention.

FIG. 13A and FIG. 13B illustrate an embodiment of the present invention.

A rotation device 1 includes a rotation section B, a guide 3' and a plurality of moving sections $4_1$ to $4_n$. In the present embodiment, the rotation device 1 also includes a driving section 2'.

The driving section 2' inputs a rotational force to the moving sections $4_i$. A rotational force from a rotational power source such as a motor is transmitted to the driving section 2' via a power transmission portion 5' and a shaft 20, so that the driving section 2' rotates about an axis O at a constant velocity, for example. The driving section 2' is axially and rotatably supported by a drum 6 via a bearing B1. The axis O of the driving section 2' is eccentric to an axis C of the drum 6. Due to such an eccentric structure, it is possible to, for example, periodically change the velocity of each moving section $4_i$ while the driving section 2' rotates.

A guide 3' is attached to the drum 6 via the rotation section B' such as a ball bearing and a rotation ring 50. In the rotation device 1 illustrated in FIG. 13A, two or more endless guides 3' are provided spaced apart from each other in the axial direction of the drum 6. As shown in FIG. 13B, a plurality of moving sections $4_1$ to $4_i$ are attached to each guide 3' so that the moving sections $4_1$ to $4_i$ are movable in the circumferential direction of the guide 3'. Therefore, each moving section $4i$ rotates around the drum 6 along with the guide 3' while additionally moving relative to the guide 3' around the drum 6 along the guide 3'.

Figure 18A:
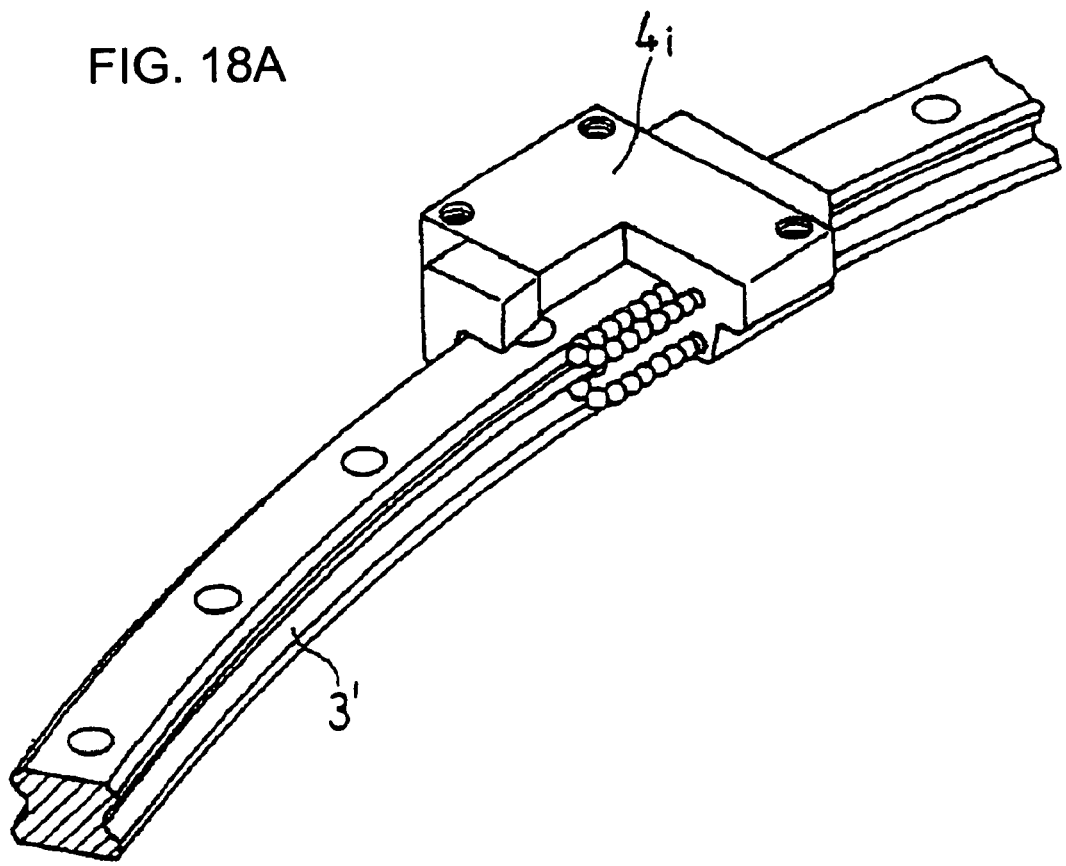
FIG. 18A is a perspective view illustrating an example of a guide and a moving section.
Figure 18B:
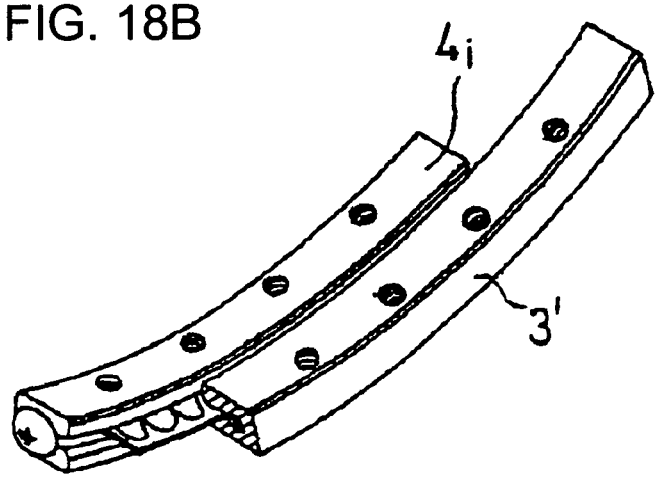
FIG. 18B is a perspective view illustrating another example of a guide and a moving section.

For the guide 3' and the moving section $4_i$, an R Guide manufactured by THK.RTM. Co., Ltd., as illustrated in FIG. 18A, or a Gonio Way manufactured by Nippon Bearing Co., Ltd., may suitably be employed. Preferably, a rolling element such as a ball or a wheel is inserted between the guide 3' and the moving section $4_i$. Each guide 3' may be a number of rails or grooves attached together in the circumferential direction of the rotation section B'. Basically, it is preferred that the reciprocating movement is a rolling movement of a bearing, or the like, but may alternatively be a sliding movement.

In FIG. 13A, a bridging section $7_i$ is provided so as to extend between each pair of moving sections $4_i$ that are spaced apart from each other in the axial direction of the drum 6. One end of an arm $70_i$ is fixed to the bridging section $7_i$, and a link $8i$ is rotatably attached to the other end of the arm $70_i$.

In the present embodiment, a controller, being capable of moving the moving sections $4i$ at a programmed velocity, is provided by the link $8i$ in combination with the eccentricity between the axes C and O. Alternatively, the controller may be provided by any other link mechanism, or a controller described in PCT International Publication WO01/44086, for example, may be used.

One end of each link $8i$ is rotatably attached to the driving section 2' via a bearing B2 and a fixed pin $8a$, and the other end of each link $8i$ is rotatably attached to the arm $70_i$ via a bearing B3 and a rotation pin $8b$. As the driving section 2 rotates at a substantially constant velocity, the fixed pin $8a$ rotates, together with the driving section 2, at a substantially constant angular velocity, while the rotation pin $8b$ rotates around the fixed pin $8a$. Thus, the angular velocity of the rotation pin $8b$ changes depending on the rotation angle of the rotation pin $8b$. Therefore, the bridging section $7_i$ integral with the rotation pin $8b$ rotates around the drum 6 while changing the interval (pitch) with respect to an adjacent bridging section $7_i$, as illustrated in FIG. 13B.

Specifically, each bridging section $7i$ rotates at a relatively low velocity while it rotates from the position of the bridging section $7_n$ to that of the bridging section $7_2$ of FIG. 13B, whereas the bridging section $7_i$ rotates at a higher velocity while it rotates from the position of the bridging section $7_2$ to that of the bridging section $7_n$. Therefore, the spacing interval (pitch) between adjacent bridging sections $7_i$ changes along with the rotation of the bridging sections $7_i$.

FIG. 14A and FIG. 14B illustrate another embodiment of the rotation device 1.

In the present embodiment, the rotation ring 50 is coupled to each rotation section B', and an attachment section $75_i$, through which a pad to be described later is inserted, is provided in a generally central portion of each bridging section $7_i$. The attachment section $75_i$ may be a space in the form of a through hole, a notch, a depression, etc.

Moreover, in the present embodiment, a groove $8A_i$ elongated in the radial direction of the drum 6 is provided, instead of the link $8i$, at an end of each bridging section $7_i$. The groove $8A_i$ is provided with the fixed pin $8a$ illustrated in FIG. 14B so that the fixed pin $8a$ is slidable in the radial direction. Therefore, the rotational velocity of the bridging section $7_i$ changes as in the previous embodiment.

In the rotation device of FIG. 14A and FIG. 14B, the velocity of the bridging section $7_i$ may be controlled by a link as illustrated in FIG. 13, or alternatively by any other controller mechanism as described above.

Figure 15A:
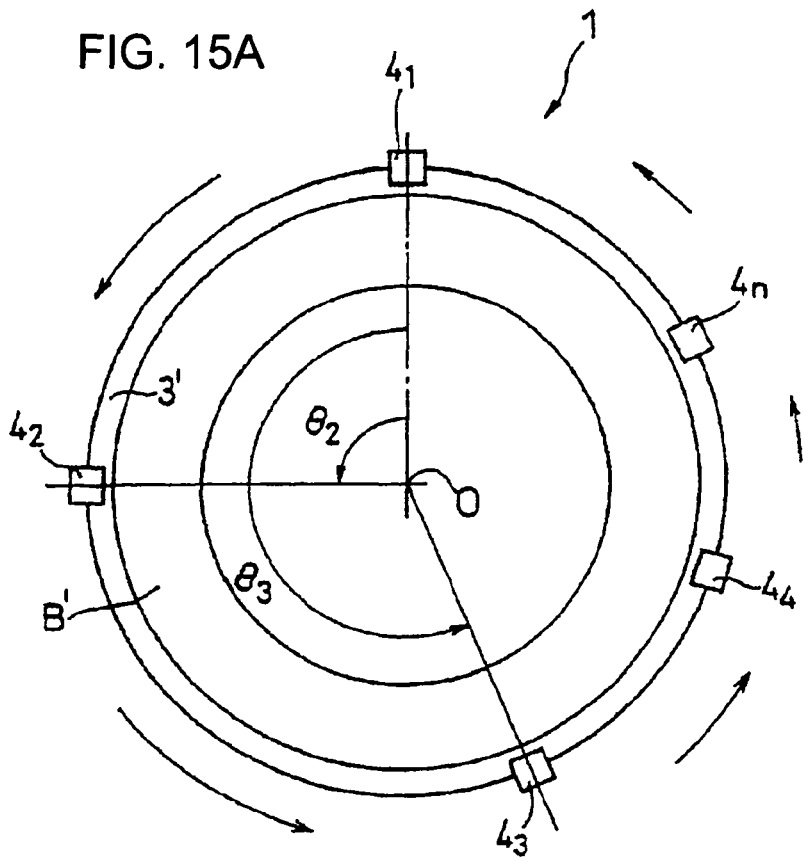
FIG. 15A is a schematic cross-sectional view illustrating a third embodiment of the rotation device of the present invention.
Figure 15B:
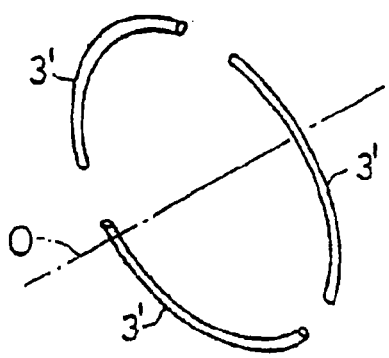
FIG. 15B is a schematic perspective view illustrating an example where a plurality of guides are provided in a concentric manner.
Figure 15C:
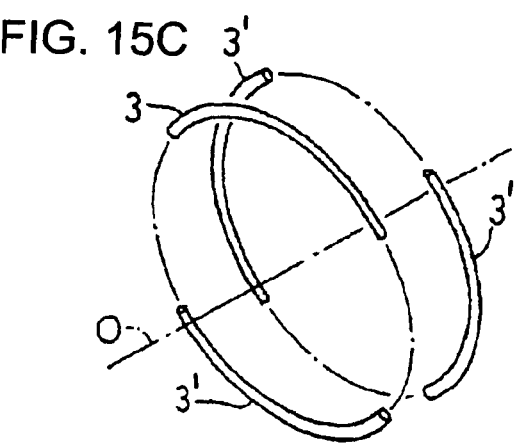
FIG. 15C is a schematic perspective view illustrating another example where a plurality of guides are provided so as to be spaced apart from each other in the axial direction of an axis O.

FIG. 15A to FIG. 15C schematically illustrate another embodiment of the rotation device of the present invention.

The rotation device 1 illustrated in FIG. 15A includes an endless guide 3', a plurality of moving sections $4_i$ moving along the guide 3', and the rotation section B. The rotation section B' allows the guide 3' to rotate about the axis of the rotation section B'.

The plurality of moving sections $4_{np}$ are arranged in the rotation allowance direction of the section B' (i.e., the direction in which the rotation section B' allows the guide 3' to rotate). Each moving section $4_i$ can move away from or toward an adjacent moving section $4_i$, and can reciprocate along the guide 3' in the direction of rotation of the rotation section B' or in the opposite direction. If the reciprocating movement is done over a particular region of the rotation section B', the guide 3' may not need to be endless. Specifically, a plurality of arc-shaped guides 3' may be arranged about the axis O of the rotation section B' so as to be spaced apart from one another in the rotation allowance direction of the rotation section B, surrounding the axis O. In such a case, each of the plurality of guides 3' includes at least one moving section that is movable in the direction of rotation of the rotation member or in the opposite direction.

The guide 3' of FIG. 15A is rotated at a predetermined rotational velocity about the axis O by a rotational force applying member (e.g., a motor or a power transmission device), which is not shown in the figure. The annular guide 3' is arranged at a predetermined position with respect to the rotation section B'. A plurality of moving sections $4_1$ to $4_i$ are movably attached to the guide 3'.

Each moving section $4_i$ can move along the guide 3' along with the rotation of the rotation section B'.

The interval between a pair of adjacent moving sections (e.g., $4_2$ and $4_3$) changes depending on the rotational position. A predetermined controller as described above may be employed to accurately control such an interval. However, a certain level of control can be provided by, for example, the gravitational acceleration acting on the moving sections $4_i$. Alternatively, a motor may be provided for each moving section $4i$ for driving the moving section $4_i$ along the guide 3' so that the moving section $4i$ rotates at an instantaneous velocity according to a rotational angle $\theta_i$.

In this embodiment, the rotation section B' may be optional. The rotation device 1 includes the endless guide 3', and a plurality of moving sections $4_i$ that move while being guided by the guide 3'. The rotation device 1 in which the guide 3' is provided with a plurality of moving sections $4_i$ may have a poor friction resistance as compared with one using ball bearings, but such a rotation device 1 can be lighter in weight than rotation devices in the prior art.

Figure 16:
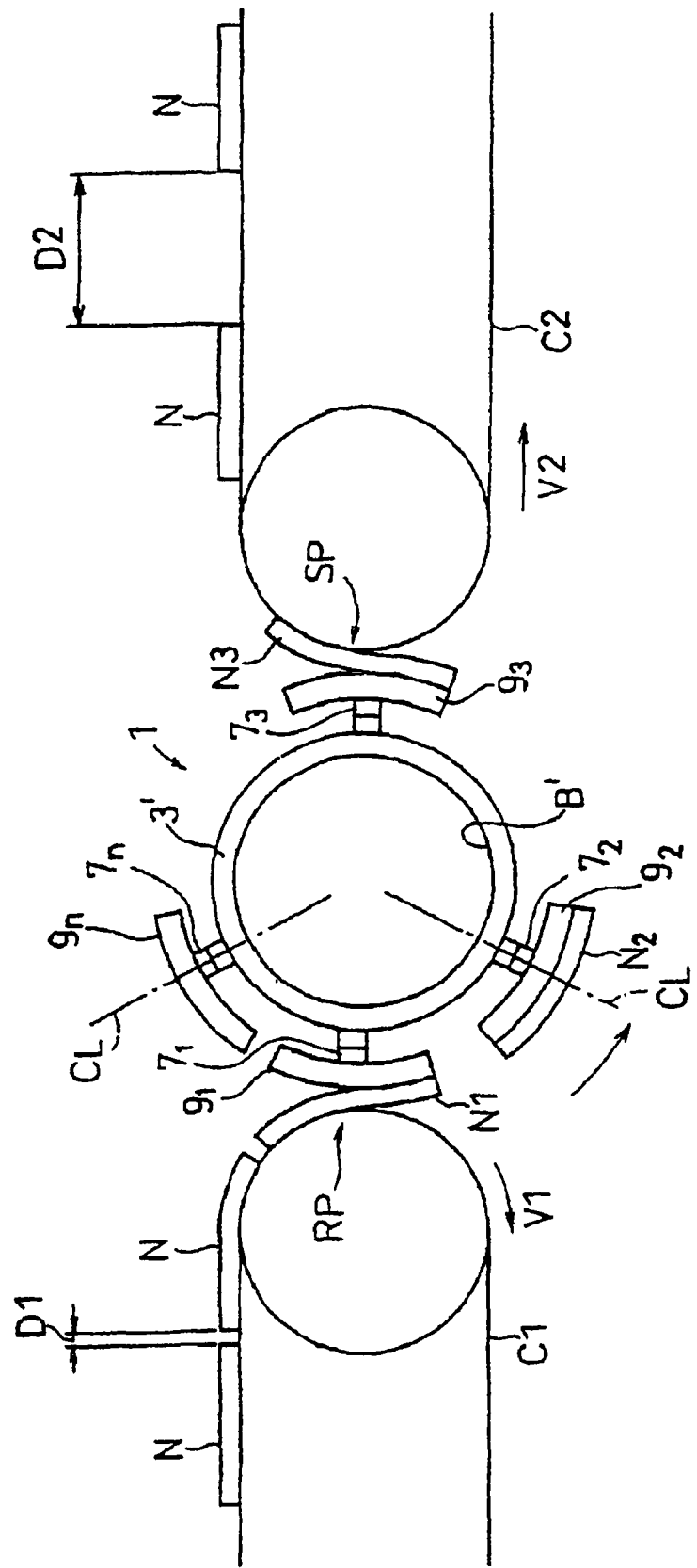
FIG. 16 is a schematic side view illustrating a transfer device.

FIG. 16 illustrates an example of a method for transferring a worn article using the rotation device 1.

The rotation device 1 includes pads $9_i$ each attracting an article N and allowing the article N to be transferred. In the rotation device 1 illustrated in FIG. 13A and FIG. 13B, each pad $9_i$ may be provided in the bridging section, or the bridging section may serve as a pad (i.e., the bridging section itself may be used as a pad). In the rotation device 1 illustrated in FIG. 14A and FIG. 14B, each pad $9_i$ may be fit into the attachment section $75_i$ of the bridging section so that the pad $9_i$ can rotate (e.g., about the direction normal to the drum 6), or the bridging section may serve as a pad. In the rotation device 1 illustrated in FIG. 15A to FIG. 15C, each pad $9_i$ may be provided in the moving section.

Each pad $9_i$ of FIG. 16 includes a plurality of suction holes for attracting the article N, and the suction holes are placed under a negative pressure to attract the article N while the pad is moving from the position of the pad $9_1$ (where the article N is received from a first conveyer C1) to the position of the pad $9_3$ (where the article N is handed over to a second conveyer C2). The pad $9_i$ may alternatively attract the article N by using an electrostatic charge, or the like.

The first conveyer C1 is provided upstream of the rotation device 1, and the second conveyer C2 is provided downstream of the rotation device 1. The first conveyer C1 transfers the articles N to the rotation device 1 at an interval D1.

For example, each pad $9_i$ rotates at a circumferential velocity V1 that is about the same as that of the first conveyer C1 from when it comes near a pickup position RP until it passes the pickup position RP, and rotates at a circumferential velocity V2 that is about the same as that of the second conveyer C2 from when it comes near a hand-over position SP until it passes the hand-over position SP. In the rotation device 1 illustrated in FIG. 16, i.e., in a case where it is desired to increase the interval between pads, the relationship between the circumferential velocities is V2>V1. However, the relationship between the circumferential velocities is V2<V1 in a case where it is desired to shorten the interval between pads. The circumferential velocity of the second conveyer is about V2.

As the article $N_1$ is transferred by the first conveyer C1 to the pickup position RP, article $N_1$ is attracted onto the pad $9_1$ and the pad $9_1$ receives the article $N_1$ at the pickup position RP. Then, the pad $9_1$ rotates toward the hand-over position SP, where the pad $9_3$ releases the article $N_3$, while gradually increasing the velocity thereof. At the hand-over position SP, the pad $9_3$ stops attracting the article $N_3$, whereby the second conveyer C2 can easily attract and receive the article $N_3$.

In a case where a portion of the pad $9_i$ is rotatably fit into the attachment section of the bridging section, the pad $9_i$ may rotate about a normal direction CL by a predetermined angle (e.g., 90°.) to change the orientation of the article $N_i$ while the pad $9_i$ moves from the pickup position RP to the hand-over position SP. The article $N_i$ may be a final or intermediate product of a worn article such as a napkin, a disposable diaper, disposable pants or a bandage, or may be a single-layer or multilayer sheet of woven fabric, non-woven fabric, a liquid permeable sheet or a liquid impermeable sheet. The intermediate product may be an absorbent or absorbents arranged over a web.

Figure 17:
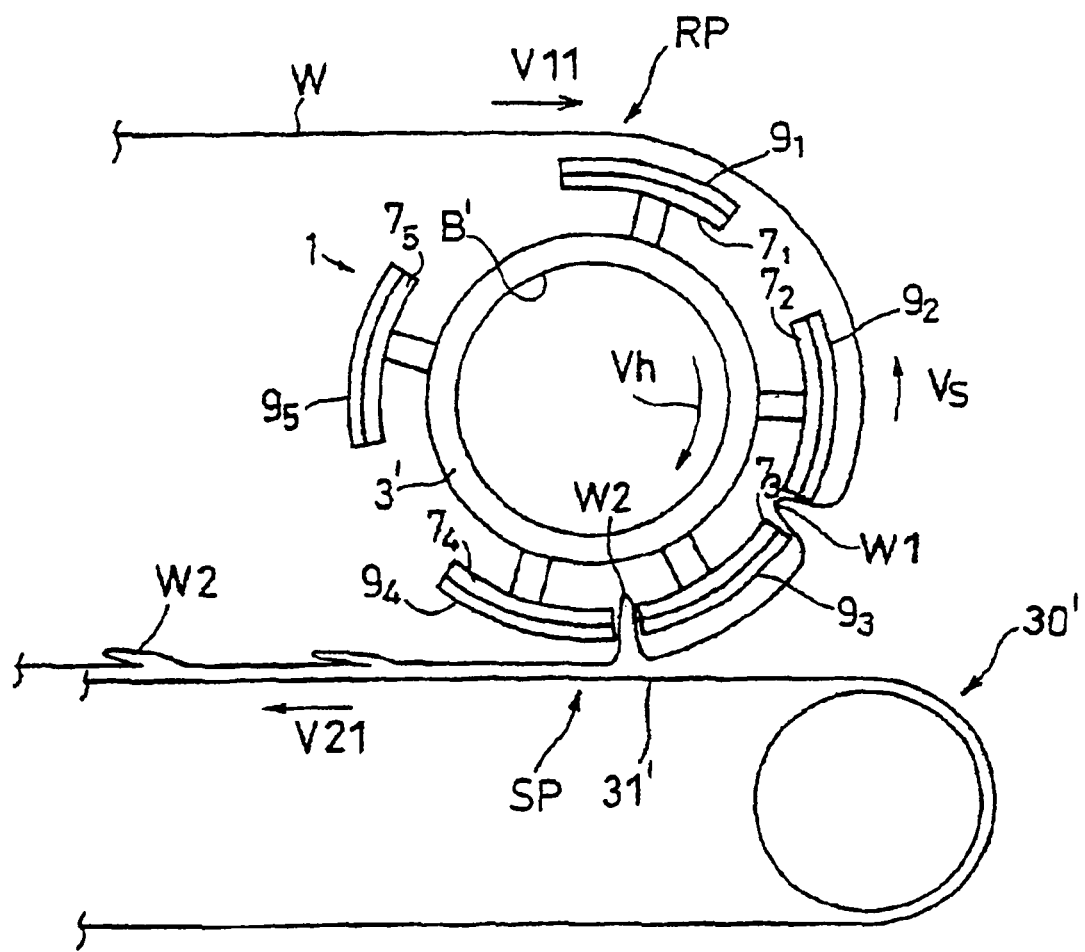
FIG. 17 is a schematic side view illustrating a folding device.

FIG. 17 illustrates an example of a method for folding a web W using the rotation device 1.

In the figure, each bridging section $7_i$ includes the pad $9_i$ for attracting the web W so that the web W can be transferred. The pad $9_i$ attracts the web W while it is moving from the position of the pad $9_1$ (where the web W is received) to the position of the pad $9_3$ (where a folded web is transferred) in FIG. 17.

The rotation device 1 forms a wheel for continuously transferring the web W, and is in contact with the surface of a belt 31' of a conveyer 30' via the web W.

The rotation device 1 picks up the web W traveling at a first velocity V11, and hands it over to the conveyer 30' traveling at a second velocity V21 (V11>V21). The belt 31' of the conveyer 30' basically transfers the web W at the circumferential velocity V21. Specifically, each pad $9_i$ rotates at the circumferential velocity V11 at the position of the pad $9_1$ (where the web W is received), and slows down to the circumferential velocity V21 by the time it reaches the position of the pad $9_3$ (where a folded web is transferred). Therefore, the interval between adjacent pads $9_i$ is shortened while the pads $9_i$ move from the pickup position RP to the hand-over position SP, thereby slackening the web W between the pads $9_i$ to form a slack portion W1.

Next, the operation will be described. The web W is supplied by being attracted onto the surface of the pad $9_1$ at the pickup position RP, and then transferred along the pads $9_i$ of the rotation device 1. While the rotation section B' rotates in the direction of an arrow Vh, the pad $9_1$ moves along the guide 3' and in the opposite direction Vs, thereby reducing the interval between the pads $9_i$. The direction Vs is defined with respect to the guide 3'. Therefore, a folded portion W2 is formed in the web W. After the formation of the folded portion W2, the pad $9_4$ stops attracting the web W, whereby the web W including folded portions W2 at a predetermined pitch is transferred onto the conveyer 30', thereby performing a so-called "Z-shaped folding process".

The rotation device for performing the Z-shaped folding process may not be the rotation device 1 described above, but may alternatively be, for example, a device described in PCT International Publication WO01/44086, or a device using any other link mechanism.

Another example of a folding device for performing the Z-shaped folding process is illustrated in FIG. 19A.

In FIG. 19A a rotation device 1A includes a plurality of pads $9_i$. At least one suction hole 10 for attracting the web W is provided in the surface of each pad $9_i$. The velocity of the pad $9_i$ is the same as that of the web W at the pickup position RP. However, at the hand-over position SP, the velocity is lower than that at the pickup position RP. Therefore, a slack portion W1 is formed in the web W. Preferably, the folding device includes a directioning section 12' so as to ensure that the slack portion W1 is folded in toward the center of the rotation device 1A.

The directioning section 12' may be, for example, a mechanism that blows out a stream of air, a mechanism that thrusts the slack portion W1 of the web toward the center of the rotation device 1A, or a mechanism that sucks the web W toward the center of the rotation device 1A by a vacuum. Where the air blowing mechanism is employed, only one directioning section 12' may be provided, or a plurality of orientation sections 12' may alternatively be provided as illustrated in FIG. 19A. Also, where the slack portion thrusting mechanism is employed, only one directioning section 12' may be provided, or a plurality of orientation sections 12' may alternatively be provided. By providing a plurality of orientation sections 12', it is possible to reliably fold in the slack portion W1 toward the center of the rotation device 1A. The width of the directioning section 12' (the length thereof in the direction perpendicular to the surface of the sheet of the figure) can be set to a value (a length in the direction perpendicular to the surface of the sheet of the figure) according to the width of the web W.

Moreover, one or more suction holes 11 may be provided on each of the side surfaces of the pads $9_i$ by which the web W is to be sandwiched, i.e., on the side surfaces of each pad that face the side surfaces of the adjacent pads, so that the slack portions W1 of the web W are laid down along the side surfaces of the pads $9_i$.

The direction in which the web is to be folded may be the direction in which the web runs or the opposite direction. For example, in a case where the circumferential velocity of the trailing one of two pads that sandwich the web therebetween is higher than that of a conveyer in the vicinity of the hand-over position SP, the web is folded by the trailing pad in the running direction. In such a case, the leading pad is only required to move so as not to interfere with the movement of the trailing pad. In a case where the circumferential velocity of the conveyer is higher than that of the leading pad in the vicinity of the hand-over position SP, the web is folded by the leading pad in the direction opposite to the running direction.

In the present embodiment, a side surface of each pad $9_i$ in the circumferential direction forms a folded portion. Specifically, the side surfaces of two adjacent pads $9_4$ and $9_5$ that are facing each other in the circumferential direction come close to each other at the hand-over position SP so as to fold in two the web W therebetween, thereby forming the folded portion W2.

An applicator (an example of a fold-holding section) 13 for applying an adhesive such as a hot melt resin may be provided on the receiving side, as illustrated in FIG. 19A. The applicator 13 applies an adhesive on one or both of another web Wo and the web W to be folded so as to bond the webs Wo and W together, thereby making it easier to maintain the shape of the folded portion W2.

Figure 20:
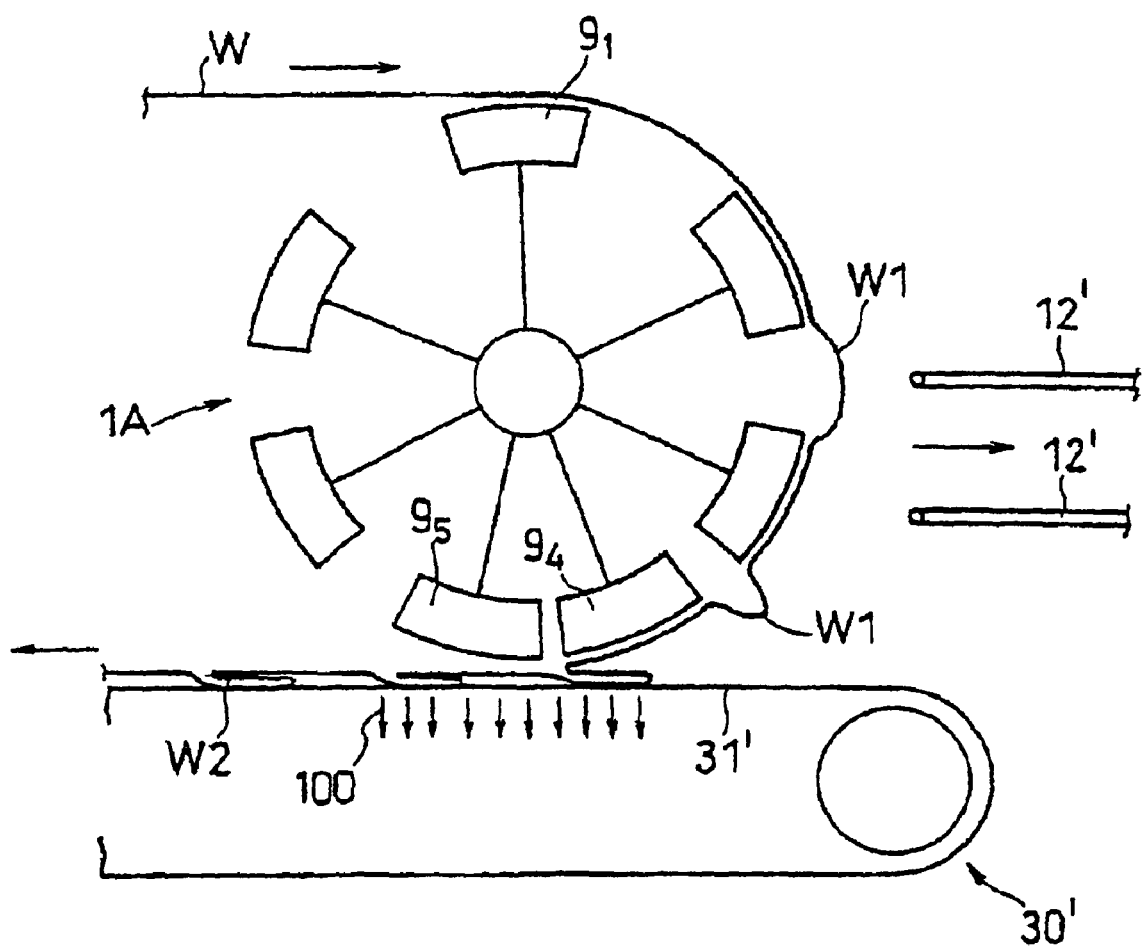
FIG. 20 is a schematic diagram illustrating another variation of a folding device.

Alternatively, in the present embodiment, a conveyer as illustrated in FIG. 20 may be used to maintain the shape of the folded portion W2.

Moreover, the directioning section 12' may suck in the slack portion W1 by a stream of air as illustrated in FIG. 20. The suction by the directioning section 12' forms the slack portion W1 into a shape that is protruding from the rotation device 1A. The suction of the web W, the number of the directioning sections, etc., may be set as those for the device of FIG. 19A.

Referring to FIG. 20, the slack portion W1 of the web is sandwiched between the pad $9_i$ and the belt 31' of the conveyer 30', thereby forming the folded portion W2. Another example of the fold-holding section provided on the receiving side may be, for example, a meshed belt 31' of the conveyer 30' capable of sucking an air therethrough by which the folded web W is received, wherein the web W is sucked by an air 100, as illustrated in FIG. 20, so as to maintain the shape of the folded portion W2. Instead of the meshed belt 31', a belt 31' including a plurality of holes therein may be used. Moreover, the fold-holding section may alternatively maintain the shape of the slack portion W1 by using an electrostatic charge, or the like.

A bellows-shaped folding device for performing a bellows-shaped folding process, which is a modified version of the Z-shaped folding process, will be described with reference to FIG. 19B to FIG. 19D. The bellows-shaped folding device is capable of folding the slackened web W at a plurality of positions.

The bellows-shaped folding device includes, in addition to the elements of the folding device of FIG. 19A, a plurality of plates $P_i$ between adjacent pads $9_{i-1}$ and $9_i$. As illustrated in FIG. 19D, the plates $P_i$ are pivotally connected to one another and to the pads $9_i$ via joints $J_i$. For example, the plate $P_1$ is pivotally connected to the pad $9_{i-1}$ via the joint $J_i$, and the adjacent plate $P_2$ is pivotally connected to the plate $P_i$ via the joint $J_2$.

Each plate $P_i$ is capable of sucking the web W. Each plate $P_i$ may include at least one suction hole, through which the web W is sucked. In such a case, each plate $P_i$ may be meshed. Moreover, the bellows-shaped folding device may have each plate $P_i$ charged with a first charge and the web with another charge that attracts the first charge, so as to attract the web W onto the plate $P_i$.

Referring to FIG. 19C, as the interval between adjacent pads $9_{i-1}$ and $9_i$ is shortened, the plurality of plates $P_i$ that have been in a spread formation are turned into a bellows-like shape. The joints $J_i$ between the plates $P_i$ may restrict the angle by which the connected plates $P_i$ can pivot in order to form a predetermined bellows-like shape in the web. For example, an elastic member 40' may be provided between the plates $P_2$ and $P_3$ as illustrated in FIG. 19D so as to restrict the angle by which the plates $P_i$ can pivot.

As the interval between adjacent pads $9_{i-1}$ and $9_i$ is shortened, the web W attracted onto the plates $P_i$ is bent so as to conform with the shape of the plates $P_i$. The slackened web W is folded so as to have top portions and bottom portions and is transferred onto the conveyer 30'.

The folded web W may be transferred onto the conveyer 30' after the interval between adjacent pads $9_{i-1}$ and $9_i$ has been shortened and before the interval therebetween reaches its maximum value. In such a case, a triangular prism-shaped wall Tw is formed as illustrated, for example, in FIGS. 22 and 23.

Figure 21:
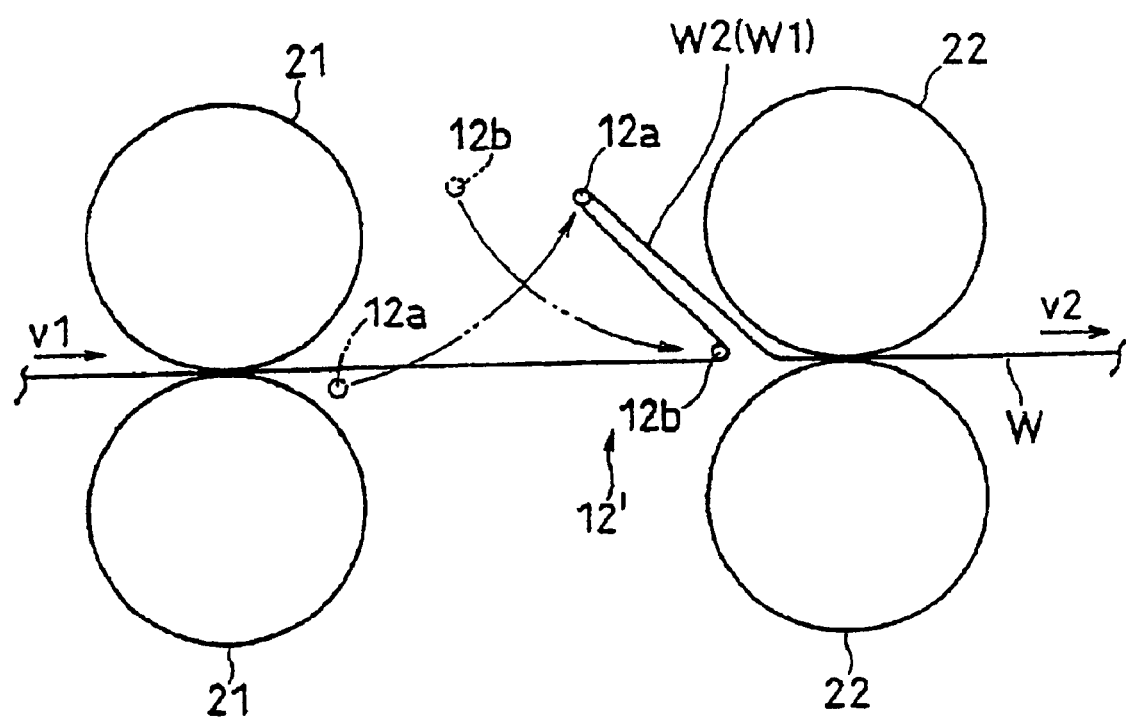
FIG. 21 is a schematic diagram illustrating another embodiment of a folding device.

FIG. 21 illustrates another example of a folding device. In the figure, a pair of first rolls 21 and 21 having a high transfer speed v1 are provided upstream, with respect to the transfer direction, along the web W, and a pair of second rolls 22 and 22 having a low transfer speed v2 are provided downstream along the web W.

Since the velocities satisfy v1>v2, the slack portion W1 is formed between the first rolls 21 and the second rolls 22. The direction in which the slack portion W1 is folded is determined by the directioning section 12. In the present embodiment, the directioning section 12 includes two bars 12a and 12b extending in the width direction of the web W. Broken lines in the figure represent the respective traces of the two bars. The second bar 12b moves after the first bar 12a moves, thereby forming the folded portion W2. Since the web W is made of a relatively light material such as non-woven fabric, pulp or a synthetic resin, the web W can easily be supported by the bars 12a and 12b with only one end thereof being fixedly supported. After the folded portion W2 is formed, the second bar 12b retracts toward the first rolls 21 before it is caught between the second rolls 22. Moreover, the first bar 12a can move in the width direction of the web W so as to extend beyond the edge of the folded portion W2.

It is possible to produce a disposable worn article, including a napkin, a diaper and pants, with a wall formed therein, by employing the "Z-shaped folding process" as described above.

Figure 22:
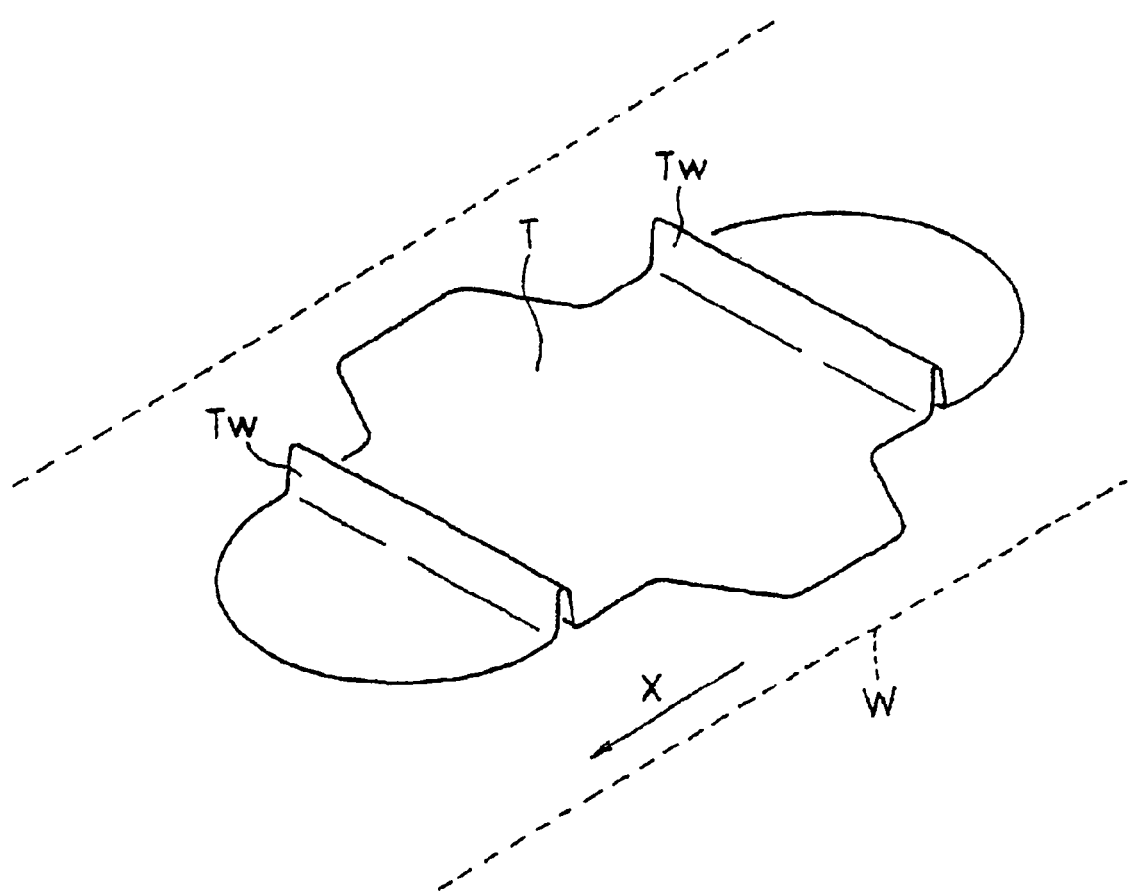
FIG. 22 is a perspective view illustrating an example of a top sheet.

FIG. 22 illustrates an example of a top sheet of a napkin, in which broken lines represent a web. In FIG. 22, the walls Tw are formed in a top sheet T so as to extend in a direction generally perpendicular to the running direction X of the top sheet T being produced. With the running direction X being a transverse direction, elongated walls Tw can be formed along the opposing sides of the napkin.

Figure 23:
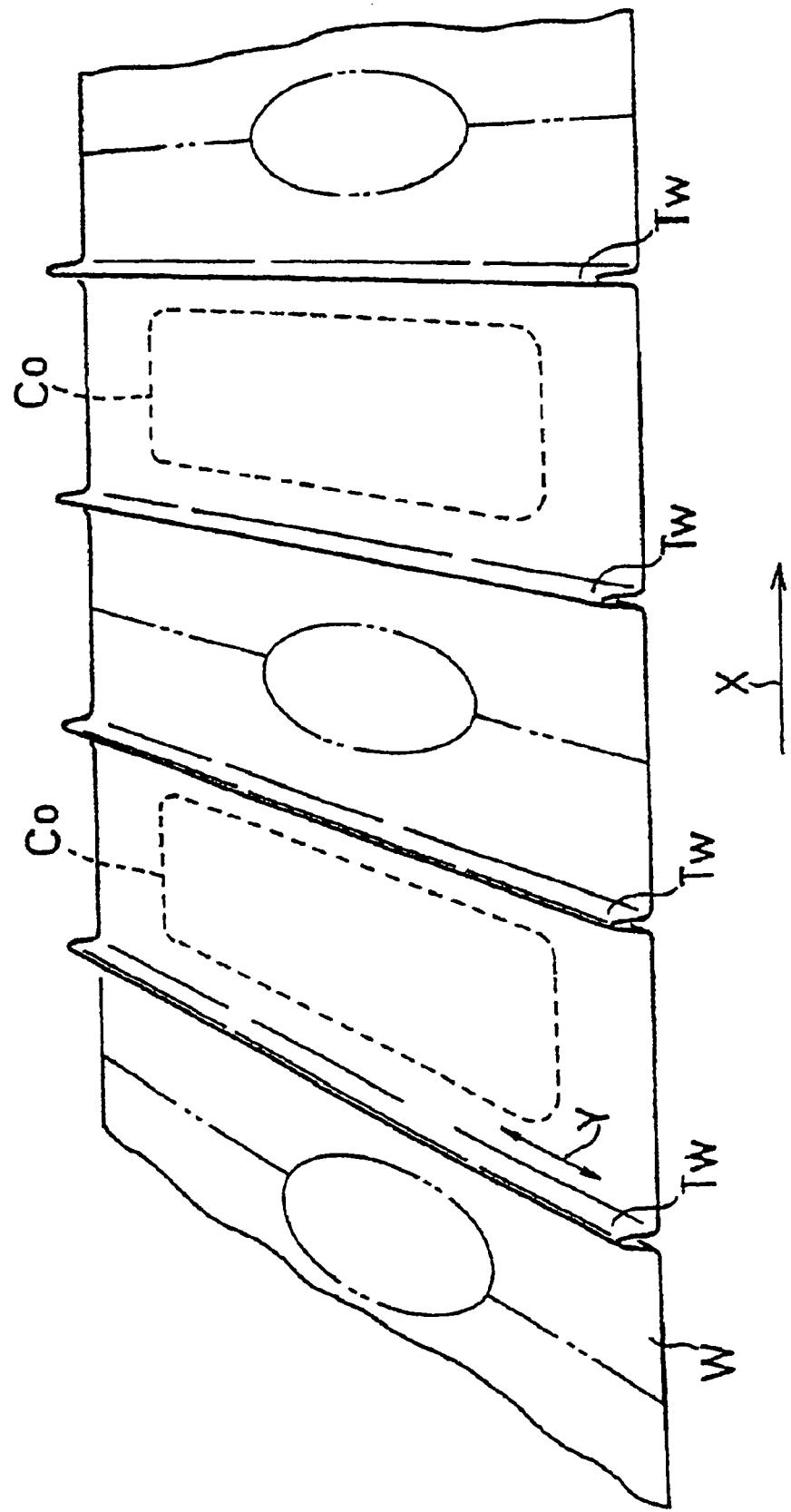
FIG. 23 is a perspective view illustrating an example of a top sheet before cutting.

FIG. 23 illustrates a top sheet (web) W of a diaper or pants before cutting. By slacking the web W using the folding method described above, the walls Tw can be formed in a direction Y transverse to a running direction X of the web W as illustrated in the figure. In other words, the longitudinal direction Y of the walls Tw is transverse to the running direction X of the web W. The longitudinal direction of an absorbent (core) Co denoted by a broken line is transverse to the running direction X of the web W (i.e., the production line is of a so-called "transverse flow" type). Therefore, it is possible to produce a diaper or pants in a transverse flow type production by cutting the web W in a direction transverse to the running direction (the X direction) as indicated by a two-dot chain line. As is well known in the art, a liquid impermeable back sheet, in addition to the absorbent Co, can be layered on the liquid permeable top sheet. The wall Tw may alternatively be formed on the absorbent Co. The wall Tw may be formed in the vicinity of an end of the absorbent Co, or a plurality of walls Tw may be formed in the vicinity of the end of the absorbent Co.

While the web is folded in a certain direction in the examples illustrated in FIG. 19A to FIG. 19D and FIG. 20, every other folded portion may be folded back in the opposite direction, for example, so as to form the walls Tw illustrated in FIG. 22 and FIG. 23.

An elastic member for making the worn article better fit to the wearer may be provided along the wall Tw. For example, a mechanism for attaching an elastic member that is extending in the direction Y transverse to the running direction X of the web W onto the web (e.g., a widening mechanism as described in Japanese Patent Application No. 12-028945) may be employed so as to provide an elastic member inside the wall Tw. The elastic member may be made of at least one flat or cord rubber.

The wall Tw of a disposable worn article such as a napkin, a diaper or pants as described above may be formed by the bellows-shaped folding process. Moreover, in a disposable worn article such as a napkin, a diaper or pants, a plurality of top portions and bottom portions may be formed on the absorbent Co through the bellows-shaped folding process. In such a case, excrement is drawn into the bottom portions, thereby reducing a leak from the worn article.

Figure 24:
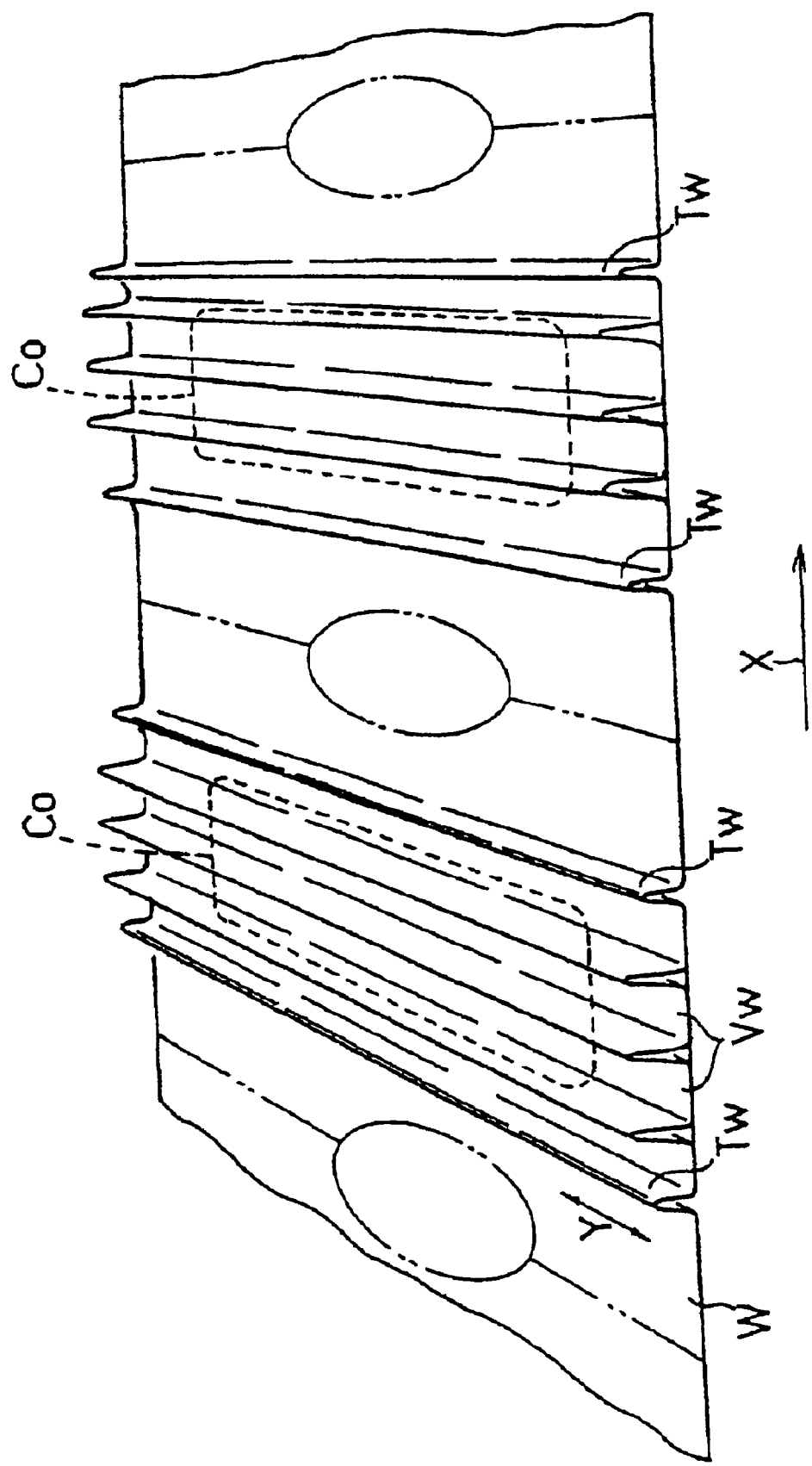
FIG. 24 is a perspective view illustrating another example of a top sheet before cutting.

FIG. 24 is a diagram illustrating an example of a plurality of walls Tw formed on each absorbent Co through the bellows-shaped folding process. The walls Tw may be positioned on the absorbent Co directly, or indirectly via a sheet, or the like. The sheet may be a continuous sheet, or at least one sheet may be layered between a plurality of walls Tw and an absorbent. In order to fix the walls Tw at predetermined positions, bottom portions Vw of the walls Tw are preferably flat. Specifically, the area over which the bottom portions Vw of the walls Tw contact the sheet or the absorbent Co is preferably 50% or more of the total area of the sheet or the absorbent Co.

Figure 25:
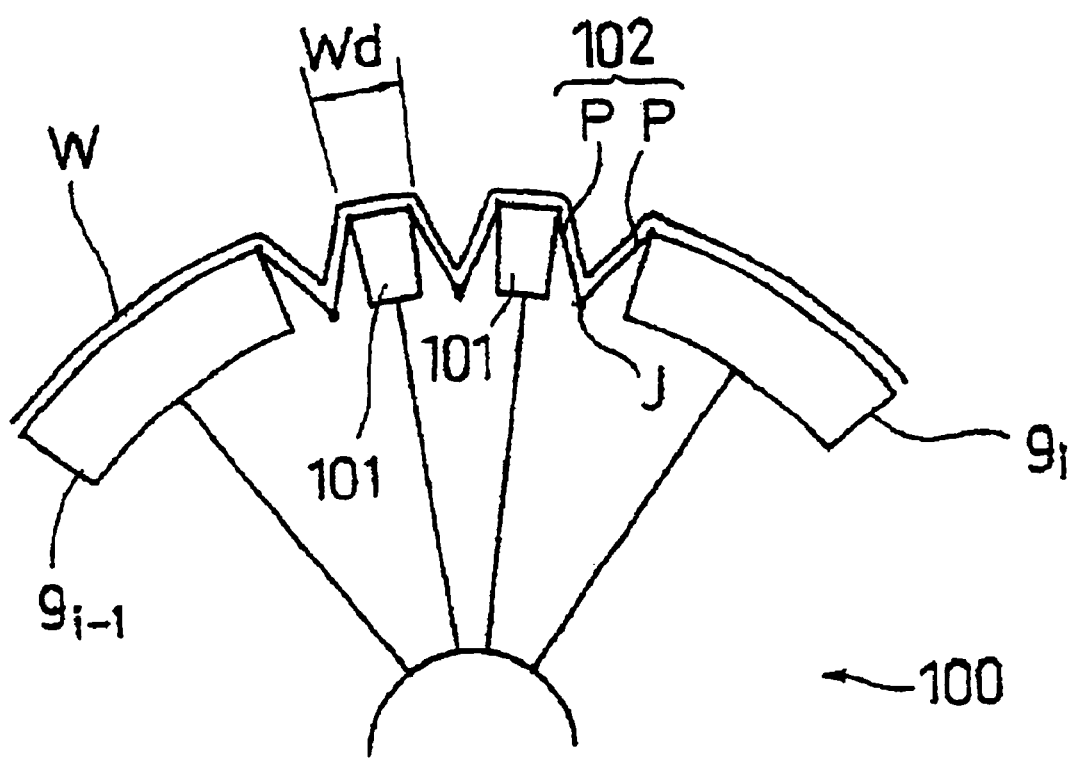
FIG. 25 is a diagram illustrating a portion of another example of a bellows-shaped folding device.

FIG. 25 is a diagram illustrating a portion of a bellows-shaped folding device 100 for forming bottom portions Vw that are generally flat. The bellows-shaped folding device 100 includes a plurality of pads $9_i$, at least one dummy pad 101, and a plurality of generally V-shaped plate pairs 102. Each of the generally V-shaped plate pairs 102 includes two plates P and P, and each plate P is capable of pivoting with respect to the other about the link between the plates P and P. One end of each generally V-shaped plate pair 102 is connected to the dummy pad 101 or the pad $9_i$.

At least one of the pads $9_i$, the dummy pad 101 and the generally V-shaped plate pair 102 is capable of sucking the web W onto the surface of the plates P and P and the surface of the top portion of the dummy pad 101. Where the width Wd of the bottom portion of the wall is 1 cm or less, the web W may be sucked by using only the pads $9_i$ and the generally V-shaped plate pairs 102. When the width Wd of the bottom portion of the wall is so small, the web W can be attracted and secured only by suction by the pads $9_i$ and the generally V-shaped plate pairs 102.

Preferably, the surface configuration of the pads $9_i$ and the dummy pads 101 is such that the surfaces of the pad $9_i$ and the dummy pad 101 contact the conveyer when handing over the folded web W to the conveyer.

Moreover, it is possible to attach at least one elastic member to a web in an intermittent manner by employing the "Z-shaped folding process". Accordingly, a disposable worn article including a web with at least one elastic member attached thereto in an intermittent manner can be produced by employing the "Z-shaped folding process".

Figure 26A:
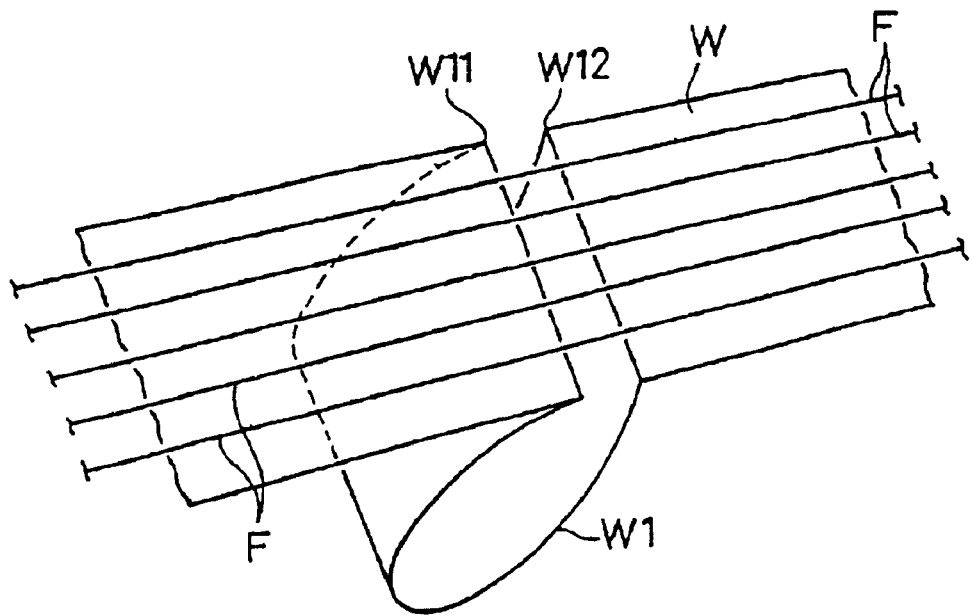
FIG. 26A is a diagram illustrating an elastic member being introduced so as to extend across a slack portion that has been obtained through a "Z-shaped folding process".

Specifically, at least one elastic member is bonded to a web, with a slack portion having been formed therein through the "Z-shaped folding process", so that the elastic member extends across the slack portion, as illustrated in FIG. 26A. Then, the elastic member F is cut off in the vicinity of a position between one edge W11 of the slack portion W1 of the web W and the other edge W12 of the slack portion W1. The elastic member F may be cut by using a straight cutter or an embossing roll. A straight cutter, an embossing roll, or the like, can cut off the elastic member through the application of heat, pressure, or a combination thereof, for example. U.S. patent application Ser. No. 09/891,034, PCT International Publication WO00/76444 and Japanese Laid-Open Patent Publication No. 2000-26015 are incorporated herein by reference, with respect to a cutting method using an embossing roll. Upon the cutting off of the elastic member, the slack of the web is eliminated.

Figure 26B:
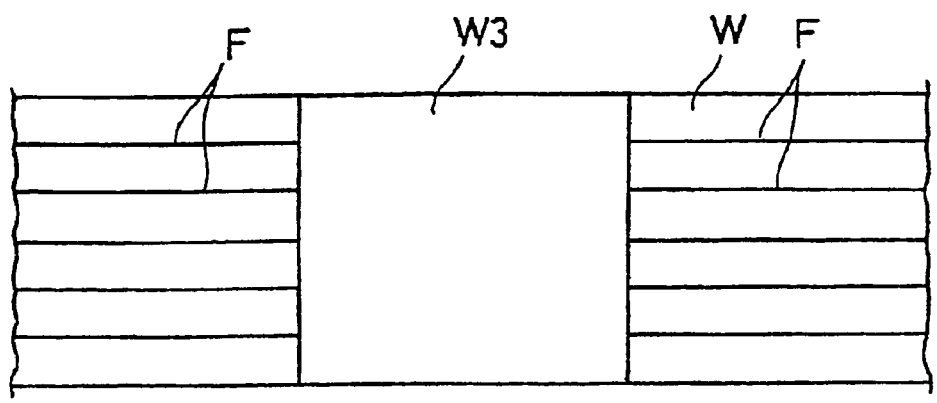
FIG. 26B is a diagram illustrating a web after cutting off the elastic member and removing the slack.

FIG. 26B is a diagram illustrating the web W after cutting off the elastic member F and eliminating the slack. In this way, the elastic member can be provided on the web W except for a portion W3 that has been a slack portion. Thus, it is possible to provide the web W with pieces of at least one elastic member F that are spaced apart from one another at a constant interval.

Figure 27:
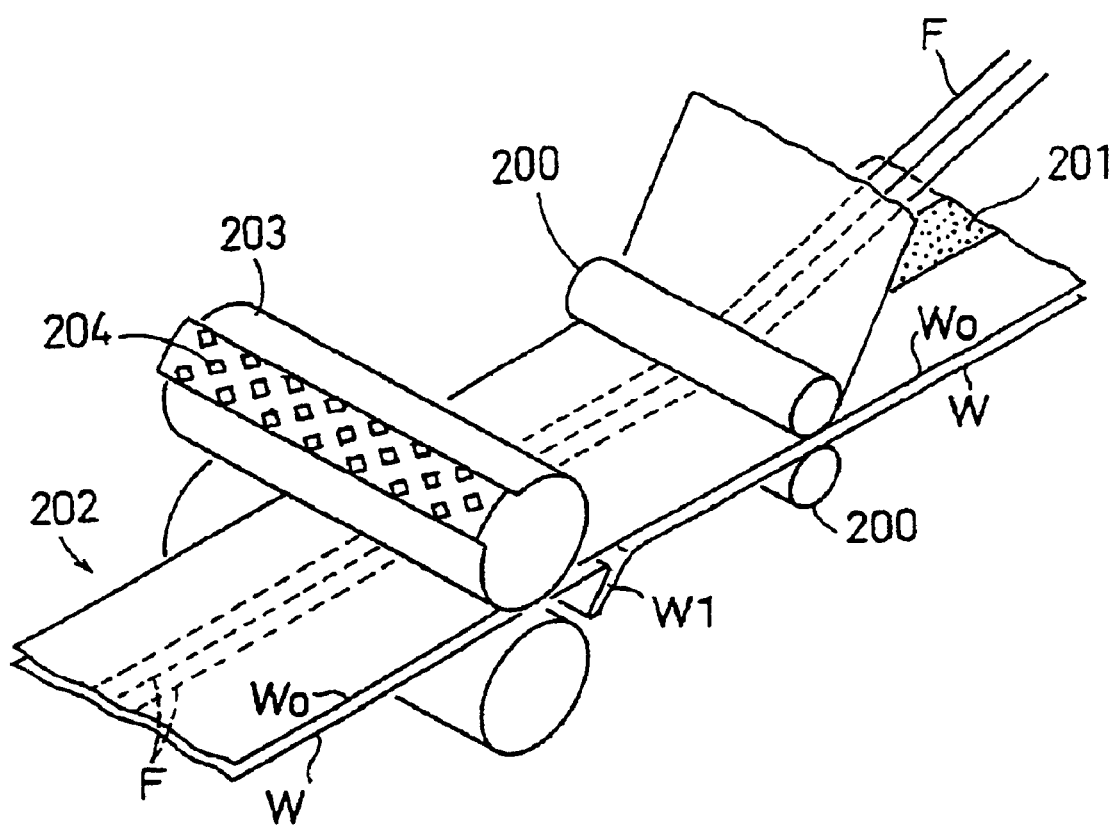
FIG. 27 is a diagram illustrating an example of a device for intermittently introducing an elastic member between a first web that has been subjected to a "Z-shaped folding process" and a second web.

An elastic member F may be sandwiched between a first web that has been subjected to the "Z-shaped folding process" and a second web. FIG. 27 illustrates an example of a device for intermittently introducing an elastic member F between a first web W that has been subjected to the "Z-shaped folding process" and a second web Wo.

The device applies an adhesive 201 on at least a portion of at least one of the first web and the second web. Then, nip rolls 200 secure the first web W, the elastic member F and the second web Wo with respect to one another. The laminate obtained by the nip rolls 200 is passed to an embossing roll 203. The embossing roll 203 is provided with a plurality of protrusions that cut off at least one the elastic member F of the laminate along with a portion of the second web Wo. The tip of each protrusion may be sharp as disclosed in U.S. patent application Ser. No. 09/891,034.

The second web Wo may be provided with a slit at each position corresponding to a slack portion W1 of the first web W. When the slack W1 of first web W is eliminated, i.e., when the laminate on which the elastic member F has been cut off is placed under a tension, the second web Wo is also cut off along the slit.

Alternatively, the second web Wo may include a slack portion. In such a case, the first web W, the elastic member F and the second web Wo are bonded together so that the position of the slack portion of the first web W corresponds to the position of the slack portion of the second web Wo. Only the elastic member F may be cut off. For example, it is possible to cut off only the elastic member F by employing an elastic member F whose melting point is lower than that of the second web Wo and embossing the laminate while heating the embossing roll 203 to a predetermined temperature. It is possible to cut off only the elastic member F with substantially no heat-induced alteration to the second web Wo if the temperature of the embossing roll 203 is higher than the melting point of the elastic member F and lower than the melting point of the second web Wo. Moreover, even when the temperature of the embossing roll 203 is higher than the melting point of the second web Wo, it is possible to cut off the elastic member before holes are created in the second web if the running velocity of the laminate is high.

Figure 28:
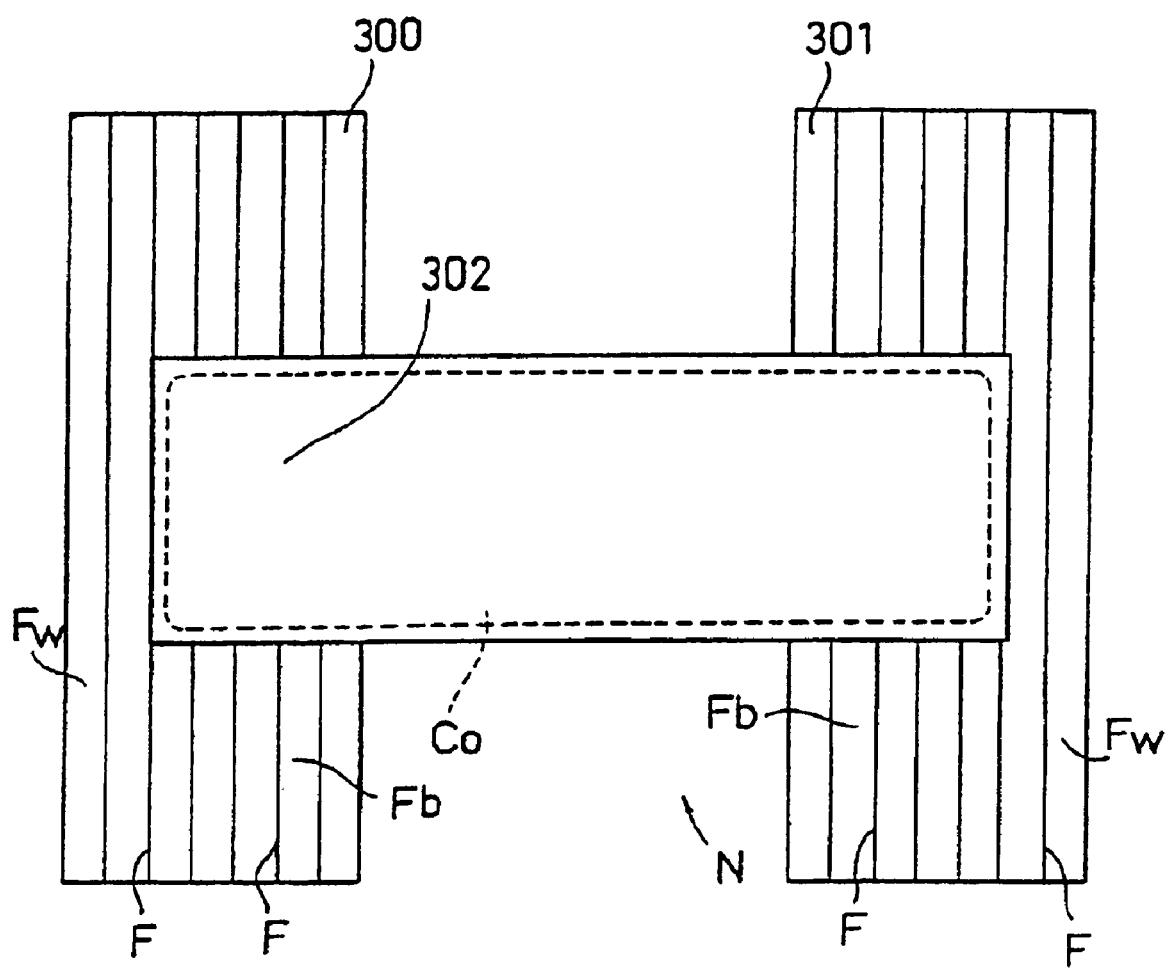
FIG. 28 is a diagram illustrating an example of a pants-shaped diaper, which is a disposable worn article, being spread out.

FIG. 28 is a diagram illustrating an example of a pants-shaped diaper N, which is a disposable worn article, being spread out. The pants-shaped diaper N includes an absorbent Co, a front flap 300 and a back flap 301. The front flap 300 and the back flap 301 include a waist gather Fw that closely fits to the wearer around the waist, and a fit gather Fb that fits to the abdominal part of the wearer. The fit gather Fb is generally absent in a portion where the pants-shaped diaper and the absorbent Co overlap with each other. If there is an elastic member F in the overlapped portion, the absorbent Co shrinks, thereby deteriorating the comfort to the wearer. The front or back flap 300, 301 can be produced by attaching an elastic member to a web in an intermittent manner by using the "Z-shaped folding process" described above. Note that the pants-shaped diaper may include a wall as described above. The worn article described above may of course be an article other than a pants-shaped diaper, such as a diaper with adhesive tapes.

The elastic member described above may be a polyurethane fiber, a natural rubber or a synthetic rubber, The polyurethane fiber may be LYCRA.RTM. manufactured by E I du Pont de Nemours and Company. The elastic member may be in the form of a cord, a string or a net, or have a flat shape. As a net-shaped elastic member, Rebound.RTM. manufactured by CONWED PLASTICS may be used.

As described above, in the rotation device of the present invention, rotation member is provided so as to allow a guide to rotate, with the guide being provided with a plurality of moving sections, whereby each moving section can slide independently. Therefore, the friction between the guide and the moving sections is significantly reduced, and thus it is possible to rotate the moving section continuously over a long period of time. Moreover, a plurality of moving sections can be provided without being spaced apart from one another in the axial direction, whereby the size of the device can be reduced.

Moreover, when a plurality of moving sections are provided in the axial direction with a bridging section extending between the moving sections, the bridging section is stabilized because the bridging section can then be supported at two positions.

Moreover, with the folding method or the folding device of the present invention, it is possible to easily and efficiently form a folded portion or a wall in a direction transverse to the direction in which the first web is transferred.

A worn article including a wall formed as described above has different characteristics from those of a worn article having a wall that is parallel to the direction in which the first web is transferred.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing a disposable worn article, comprising the steps of: forming a slack portion in a web; placing at least one elastic member so that the elastic member extends in a running direction of the web and across the slack portion, and fixing at least a portion of the elastic member; cutting off the elastic member at the slack portion; and attaching an absorbent to the web at the slack portion.

2. A method for producing a disposable worn article according to claim 1, wherein the elastic member is fixed in the fixing step by being sandwiched between the web and another web.

3. A method for producing a disposable worn article according to claim 2, wherein a slack portion is provided in the other web so that a position of the slack portion of the web corresponds to a position of the slack portion of the other web.

4. A method for producing a disposable worn article according to claim 2, wherein the other web includes a slit at a position corresponding to the slack portion of the web.

5. A method for producing a disposable worn article according to claim 1, further comprising the step of eliminating a slack in the web after the step of cutting off the elastic member.

6. A method for producing a disposable worn article according to claim 2, further comprising the step of eliminating a slack in the web after the step of cutting off the elastic member.

7. A method for producing a disposable worn article according to claim 3, further comprising the step of eliminating a slack in the web after the step of cutting off the elastic member.

8. A method for producing a disposable worn article, comprising the steps of: forming a slack portion in a web while rotating the web at a constant radius with a plurality of movable sections radially restrained by a guide member to rotate in a circular path; placing at least one elastic member so that the elastic member extends in a running direction of the web and across the slack portion, and fixing at least a portion of the elastic member; and cutting off the elastic member at the slack portion.

9. A method for producing a disposable worn article according to claim 8, wherein the elastic member is fixed in the fixing step by being sandwiched between the web and another web.

10. A method for producing a disposable worn article according to claim 9, wherein a slack portion is provided in the other web so that a position of the slack portion of the web corresponds to a position of the slack portion of the other web.

11. A method for producing a disposable worn article according to claim 9, wherein the other web includes a slit at a position corresponding to the slack portion of the web.

12. A method for producing a disposable worn article according to claim 8, further comprising the step of eliminating a slack in the web after the step of cutting off the elastic member.

13. A method for producing a disposable worn article according to claim 9, further comprising the step of eliminating a slack in the web after the step of cutting off the elastic member.

14. A method for producing a disposable worn article according to claim 10, further comprising the step of eliminating a slack in the web after the step of cutting off the elastic member.

15. A method as set forth in claim 1, wherein the attaching an absorbent step further comprises attaching the absorbent to the web in a portion of the web between adjacent elastic pieces formed by cutting the elastic at the slack portion.

16. A method for producing a disposable worn article according to claim 8, wherein at least a portion of the guide member is ring-shaped.

* * * * *